United States Patent
Reed

(10) Patent No.: US 8,993,742 B2
(45) Date of Patent: Mar. 31, 2015

(54) TUBULO-VESICULAR STRUCTURE LOCALIZATION SIGNALS

(75) Inventor: Thomas David Reed, Blacksburg, VA (US)

(73) Assignee: Intrexon Corporation, Blacksburg, VA (US)

( * ) Notice: Subject to any disclaimer, the term of this patent is extended or adjusted under 35 U.S.C. 154(b) by 413 days.

(21) Appl. No.: 12/973,624

(22) Filed: Dec. 20, 2010

(65) Prior Publication Data

US 2011/0195504 A1 Aug. 11, 2011

Related U.S. Application Data

(63) Continuation of application No. 11/999,143, filed on Dec. 4, 2007, now abandoned.

(60) Provisional application No. 60/868,538, filed on Dec. 4, 2006.

(51) Int. Cl.
| | | |
|---|---|---|
| *C07H 21/04* | (2006.01) | |
| *C12N 15/62* | (2006.01) | |
| *C12P 21/00* | (2006.01) | |
| *C12P 21/02* | (2006.01) | |
| *C07K 14/47* | (2006.01) | |

(52) U.S. Cl.
CPC .................................. *C07K 14/47* (2013.01)
USPC ...... 536/23.4; 435/69.1; 435/70.1; 435/320.1

(58) Field of Classification Search
USPC ............ 435/69.1, 69.7, 70.1, 320.1; 536/23.4
See application file for complete search history.

(56) References Cited

U.S. PATENT DOCUMENTS

| | | | | |
|---|---|---|---|---|
| 5,756,307 | A * | 5/1998 | Uhl et al. ...................... | 435/69.1 |
| 5,919,667 | A * | 7/1999 | Gage et al. .................... | 435/91.4 |
| 7,939,268 | B2 * | 5/2011 | Frantz et al. .................. | 435/7.1 |
| 2003/0188345 | A1 * | 10/2003 | Heim et al. ................... | 800/294 |
| 2004/0185556 | A1 | 9/2004 | Reed | |
| 2008/0050808 | A1 | 2/2008 | Reed et al. | |
| 2010/0293625 | A1 * | 11/2010 | Reed .............................. | 800/18 |

FOREIGN PATENT DOCUMENTS

| | | | |
|---|---|---|---|
| WO | WO 2005/040336 A2 | 5/2005 | |
| WO | WO 2005/116231 A1 | 12/2005 | |

OTHER PUBLICATIONS

Epand et al., Biochimica et Biophysica Acta 1614 (2003) 116-121 Biochimica et Biophysica Acta 1614 (2003) 116-121.*
Claims for U.S. Appl. No. 12/681,609, filed Apr. 10, 2014 corresponding to USPub 2010/0293625.*

* cited by examiner

*Primary Examiner* — Maria Leavitt
(74) *Attorney, Agent, or Firm* — Sterne, Kessler, Goldstein & Fox P.L.L.C.

(57) ABSTRACT

The invention relates to polarized cell tubulo-vesicular structure localization signals. The localization signals are utilized as research tools or are linked to polypeptides of interest or therapeutic molecules. Disclosed are methods of making and using polypeptides and modified polypeptides as signals to localize therapeutics, experimental compounds, peptides, proteins and/or other macromolecules to the tubulo-vesicular structures of polarized cells. The polypeptides of the invention optionally include linkage to reporters, epitopes and/or other experimental or therapeutic molecules. The invention also encompasses polynucleotides encoding the localization signals and vectors comprising these polynucleotides.

16 Claims, 15 Drawing Sheets

| PROMOTER | POLYPEPTIDE OF INTEREST | LOCALIZATION SIGNAL | STOP | POLY-A |

FIGURE 4A

| PROMOTER | LOCALIZATION SIGNAL | POLYPEPTIDE OF INTEREST | STOP | POLY-A |

FIGURE 4B

| PROMOTER | LOCALIZATION SIGNAL 1 | POLYPEPTIDE OF INTEREST | LOCALIZATION SIGNAL 2 | STOP | POLY-A |

FIGURE 4C

| PROMOTER | POLYPEPTIDE OF INTEREST | OPTIONAL REPORTER | LOCALIZATION SIGNAL | STOP | POLY-A |

FIGURE 4D

| PROMOTER | LOCALIZATION SIGNAL 1 | OPTIONAL EPITOPE | POLYPEPTIDE OF INTEREST | LOCALIZATION SIGNAL 2 | STOP | POLY-A |

FIGURE 4E

| PROMOTER | LOCALIZATION SIGNAL | POLYPEPTIDE OF INTEREST | OPTIONAL EPITOPE | STOP | POLY-A |

FIGURE 4F

| PROMOTER | LOCALIZATION SIGNAL | REPORTER | STOP | POLY-A |

FIGURE 4G

| PROMOTER | REPORTER | LOCALIZATION SIGNAL | STOP | POLY-A |

FIGURE 4H

VVN-8595 RG2+(PLA-5'+CAT+FLAG+PLA1-3')+SV40pA

VVN-8596 RG2+(PLA1-5'+CAT+FLAG+PLA1-3')+hGHpA

VVN-8598 RG2+(PLB1-5'+CAT+HA+PLB1-3')+SV40pA

WN-8599 RG2+(PLB1-5'+CAT+HA+PLB1-3')+hGHpA

SEQUENCE LISTING

```
<160> NUMBER OF SEQ ID NOS: 8

<210> SEQ ID NO 1
<211> LENGTH: 620
<212> TYPE: PRT
<213> ORGANISM: Homo sapiens

<400> SEQUENCE: 1

Met Ser Lys Ser Lys Cys Ser Val Gly Leu Met Ser Ser Val Val Ala
1               5                   10                  15

Pro Ala Lys Glu Pro Asn Ala Val Gly Pro Lys Glu Val Glu Leu Ile
            20                  25                  30

Leu Val Met Glu Gln Asn Gly Val Gln Leu Thr Ser Ser Thr Leu Thr
        35                  40                  45

Asn Pro Arg Gln Ser Pro Val Glu Ala Gln Asp Arg Glu Thr Trp Gly
    50                  55                  60

Lys Lys Ile Asp Phe Leu Leu Ser Val Ile Gly Phe Ala Val Asp Leu
65                  70                  75                  80

Ala Asn Val Trp Arg Phe Pro Tyr Leu Cys Tyr Lys Asn Gly Gly Gly
                85                  90                  95

Ala Phe Leu Val Pro Tyr Leu Leu Phe Met Val Ile Ala Gly Met Pro
            100                 105                 110

Leu Phe Tyr Met Glu Leu Ala Leu Gly Gln Phe Asn Arg Glu Gly Ala
        115                 120                 125

Ala Gly Val Trp Lys Ile Cys Pro Ile Leu Lys Gly Val Gly Phe Thr
    130                 135                 140

Val Ile Leu Ile Ser Leu Tyr Val Gly Phe Phe Tyr Asn Val Ile Ile
145                 150                 155                 160

Ala Trp Ala Leu His Tyr Leu Phe Ser Ser Phe Thr Thr Glu Leu Pro
                165                 170                 175

Trp Ile His Cys Asn Asn Ser Trp Asn Ser Pro Asn Cys Ser Asp Ala
            180                 185                 190

His Pro Gly Asp Ser Ser Gly Asp Ser Ser Gly Leu Asn Asp Thr Phe
        195                 200                 205

Gly Thr Thr Pro Ala Ala Glu Tyr Phe Glu Arg Gly Val Leu His Leu
    210                 215                 220

His Gln Ser His Gly Ile Asp Asp Leu Gly Pro Pro Arg Trp Gln Leu
225                 230                 235                 240

Thr Ala Cys Leu Val Leu Val Ile Val Leu Leu Tyr Phe Ser Leu Trp
                245                 250                 255

Lys Gly Val Lys Thr Ser Gly Lys Val Val Trp Ile Thr Ala Thr Met
            260                 265                 270
```

```
Pro Tyr Val Val Leu Thr Ala Leu Leu Arg Val Thr Leu Pro
            275                 280                 285

Gly Ala Ile Asp Gly Ile Arg Ala Tyr Leu Ser Val Asp Phe Tyr Arg
        290                 295                 300

Leu Cys Glu Ala Ser Val Trp Ile Asp Ala Ala Thr Gln Val Cys Phe
305                 310                 315                 320

Ser Leu Gly Val Gly Phe Gly Val Leu Ile Ala Phe Ser Ser Tyr Asn
                325                 330                 335

Lys Phe Thr Asn Asn Cys Tyr Arg Asp Ala Ile Val Thr Thr Ser Ile
                340                 345                 350

Asn Cys Leu Thr Ser Phe Ser Ser Gly Phe Val Val Phe Ser Phe Leu
                355                 360                 365

Gly Tyr Met Ala Gln Lys His Ser Val Pro Ile Gly Asp Val Ala Lys
            370                 375                 380

Asp Gly Pro Gly Leu Ile Phe Ile Ile Tyr Pro Glu Ala Ile Ala Thr
385                 390                 395                 400

Leu Pro Leu Ser Ser Ala Trp Ala Val Val Phe Phe Ile Met Leu Leu
                405                 410                 415

Thr Leu Gly Ile Asp Ser Ala Met Gly Gly Met Glu Ser Val Ile Thr
            420                 425                 430

Gly Leu Ile Asp Glu Phe Gln Leu Leu His Arg His Arg Glu Leu Phe
        435                 440                 445

Thr Leu Phe Ile Val Leu Ala Thr Phe Leu Leu Ser Leu Phe Cys Val
    450                 455                 460

Thr Asn Gly Gly Ile Tyr Val Phe Thr Leu Leu Asp His Phe Ala Ala
465                 470                 475                 480

Gly Thr Ser Ile Leu Phe Gly Val Leu Ile Glu Ala Ile Gly Val Ala
                485                 490                 495

Trp Phe Tyr Gly Val Gly Gln Phe Ser Asp Asp Ile Gln Gln Met Thr
            500                 505                 510

Gly Gln Arg Pro Ser Leu Tyr Trp Arg Leu Cys Trp Lys Leu Val Ser
        515                 520                 525

Pro Cys Phe Leu Leu Phe Val Val Val Ser Ile Val Thr Phe Arg
530                 535                 540

Pro Pro His Tyr Gly Ala Tyr Ile Phe Pro Asp Trp Ala Asn Ala Leu
545                 550                 555                 560

Gly Trp Val Ile Ala Thr Ser Ser Met Ala Met Val Pro Ile Tyr Ala
                565                 570                 575

Ala Tyr Lys Phe Cys Ser Leu Pro Gly Ser Phe Arg Glu Lys Leu Ala
            580                 585                 590

Tyr Ala Ile Ala Pro Glu Lys Asp Arg Glu Leu Val Asp Arg Gly Glu
            595                 600                 605

Val Arg Gln Phe Thr Leu Arg His Trp Leu Lys Val
610                 615                 620

<210> SEQ ID NO 2
<211> LENGTH: 627
<212> TYPE: PRT
<213> ORGANISM: rat

<400> SEQUENCE: 2

Met Thr Ala Glu Gln Ala Leu Pro Leu Gly Asn Gly Lys Ala Ala Glu
1               5                   10                  15

Glu Ala Arg Gly Ser Glu Ala Leu Gly Gly Gly Gly Gly Ala Ala
            20                  25                  30
```

```
Gly Thr Arg Glu Ala Arg Asp Lys Ala Val His Glu Arg Gly His Trp
         35                  40                  45

Asn Asn Lys Val Glu Phe Val Leu Ser Val Ala Gly Glu Ile Ile Gly
 50                  55                  60

Leu Gly Asn Val Trp Arg Phe Pro Tyr Leu Cys Tyr Lys Asn Gly Gly
 65                  70                  75                  80

Gly Ala Phe Leu Ile Pro Tyr Val Val Phe Ile Cys Cys Gly Ile
                     85                  90                  95

Pro Val Phe Phe Leu Glu Thr Ala Leu Gly Gln Phe Thr Ser Glu Gly
                100                 105                 110

Gly Ile Thr Cys Trp Arg Arg Val Cys Pro Leu Phe Glu Gly Ile Gly
                115                 120                 125

Tyr Ala Thr Gln Val Ile Glu Ala His Leu Asn Val Tyr Tyr Ile Ile
                130                 135                 140

Ile Leu Ala Trp Ala Ile Phe Tyr Leu Ser Asn Cys Phe Thr Thr Glu
145                 150                 155                 160

Leu Pro Trp Ala Thr Cys Gly His Glu Trp Asn Thr Glu Lys Cys Val
                165                 170                 175

Glu Phe Gln Lys Leu Asn Phe Ser Asn Tyr Ser His Val Ser Leu Gln
                180                 185                 190

Asn Ala Thr Ser Pro Val Met Glu Phe Trp Glu Arg Arg Val Leu Ala
                195                 200                 205

Ile Ser Asp Gly Ile Glu His Ile Gly Asn Leu Arg Trp Glu Leu Ala
210                 215                 220

Leu Cys Leu Leu Ala Ala Trp Thr Ile Cys Tyr Phe Cys Ile Trp Lys
225                 230                 235                 240

Gly Thr Lys Ser Thr Gly Lys Val Val Tyr Val Thr Ala Thr Phe Pro
                245                 250                 255

Tyr Ile Met Leu Leu Ile Leu Leu Ile Arg Gly Val Thr Leu Pro Gly
                260                 265                 270

Ala Ser Glu Gly Ile Lys Phe Tyr Leu Tyr Pro Asp Leu Ser Arg Leu
                275                 280                 285

Ser Asp Pro Gln Val Trp Val Asp Ala Gly Thr Gln Ile Phe Phe Ser
290                 295                 300

Tyr Ala Ile Cys Leu Gly Cys Leu Thr Ala Leu Gly Ser Tyr Asn Asn
305                 310                 315                 320

Tyr Asn Asn Asn Cys Tyr Arg Asp Cys Ile Met Leu Cys Cys Leu Asn
                325                 330                 335

Ser Gly Thr Ser Phe Val Ala Gly Phe Ala Ile Phe Ser Val Leu Gly
                340                 345                 350

Phe Met Ala Tyr Glu Gln Gly Val Pro Ile Ala Glu Val Ala Glu Ser
                355                 360                 365

Gly Pro Gly Leu Ala Phe Ile Ala Tyr Pro Lys Ala Val Thr Met Met
                370                 375                 380

Pro Leu Ser Pro Leu Trp Ala Thr Leu Phe Phe Met Met Leu Ile Phe
385                 390                 395                 400

Leu Gly Leu Asp Ser Gln Phe Val Cys Val Glu Ser Leu Val Thr Ala
                405                 410                 415

Val Val Asp Met Tyr Pro Lys Val Phe Arg Arg Gly Tyr Arg Arg Glu
                420                 425                 430

Leu Leu Ile Leu Ala Leu Ser Ile Val Ser Tyr Phe Leu Gly Leu Val
                435                 440                 445
```

Met Leu Thr Glu Gly Gly Met Tyr Ile Phe Gln Leu Phe Asp Ser Tyr
450                 455                 460

Ala Ala Ser Gly Met Cys Leu Leu Phe Val Ala Ile Phe Glu Cys Val
465                 470                 475                 480

Cys Ile Gly Trp Val Tyr Gly Ser Asn Arg Phe Tyr Asp Asn Ile Glu
                485                 490                 495

Asp Met Ile Gly Tyr Arg Pro Leu Ser Leu Ile Lys Trp Cys Trp Lys
                500                 505                 510

Val Val Thr Pro Gly Ile Cys Ala Gly Ile Phe Ile Phe Leu Val
                515                 520                 525

Lys Tyr Lys Pro Leu Lys Tyr Asn Asn Val Tyr Thr Tyr Pro Ala Trp
530                 535                 540

Gly Tyr Gly Ile Gly Trp Leu Met Ala Leu Ser Ser Met Leu Cys Ile
545                 550                 555                 560

Pro Leu Trp Ile Phe Ile Lys Leu Trp Lys Thr Gly Thr Leu Pro
                565                 570                 575

Glu Lys Leu Gln Lys Leu Thr Val Pro Ser Ala Asp Leu Lys Met Arg
                580                 585                 590

Gly Lys Leu Gly Ala Ser Pro Arg Met Val Thr Val Asn Asp Cys Glu
                595                 600                 605

Ala Lys Val Lys Gly Asp Gly Thr Ile Ser Ala Ile Thr Glu Lys Glu
610                 615                 620

Thr His Phe
625

<210> SEQ ID NO 3
<211> LENGTH: 617
<212> TYPE: PRT
<213> ORGANISM: Homo sapiens

<400> SEQUENCE: 3

Met Leu Leu Ala Arg Met Asn Pro Gln Val Gln Pro Glu Asn Asn Gly
1               5                   10                  15

Ala Asp Thr Gly Pro Glu Gln Pro Leu Arg Ala Arg Lys Thr Ala Glu
                20                  25                  30

Leu Leu Val Val Lys Glu Arg Asn Gly Val Gln Cys Leu Leu Ala Pro
                35                  40                  45

Arg Asp Gly Asp Ala Gln Pro Arg Glu Thr Trp Gly Lys Lys Ile Asp
50                  55                  60

Phe Leu Leu Ser Val Val Gly Phe Ala Val Asp Leu Ala Asn Val Trp
65                  70                  75                  80

Arg Phe Pro Tyr Leu Cys Tyr Lys Asn Gly Gly Gly Ala Phe Leu Ile
                85                  90                  95

Pro Tyr Thr Leu Phe Leu Ile Ile Ala Gly Met Pro Leu Phe Tyr Met
                100                 105                 110

Glu Leu Ala Leu Gly Gln Tyr Asn Arg Glu Gly Ala Ala Thr Val Trp
                115                 120                 125

Lys Ile Cys Pro Phe Phe Lys Gly Val Gly Tyr Ala Val Ile Leu Ile
                130                 135                 140

Ala Leu Tyr Val Gly Phe Tyr Tyr Asn Val Ile Ala Trp Ser Leu
145                 150                 155                 160

Tyr Tyr Leu Phe Ser Ser Phe Thr Leu Asn Leu Pro Trp Thr Asp Cys
                165                 170                 175

Gly His Thr Trp Asn Ser Pro Asn Cys Thr Asp Pro Lys Leu Leu Asn
                180                 185                 190

```
Gly Ser Val Leu Gly Asn His Thr Lys Tyr Ser Lys Tyr Lys Phe Thr
            195                 200                 205

Pro Ala Ala Glu Phe Tyr Glu Arg Gly Val Leu His Leu His Glu Ser
210                 215                 220

Ser Gly Ile His Asp Ile Gly Leu Pro Gln Trp Gln Leu Leu Leu Cys
225                 230                 235                 240

Leu Met Val Val Ile Val Leu Tyr Phe Ser Leu Trp Lys Gly Val
                245                 250                 255

Lys Thr Ser Gly Lys Val Val Trp Ile Thr Ala Thr Leu Pro Tyr Phe
                260                 265                 270

Val Leu Phe Val Leu Leu Val His Gly Val Thr Leu Pro Gly Ala Ser
            275                 280                 285

Asn Gly Ile Asn Ala Tyr Leu His Ile Asp Phe Tyr Arg Leu Lys Glu
            290                 295                 300

Ala Thr Val Trp Ile Asp Ala Ala Thr Gln Ile Phe Phe Ser Leu Gly
305                 310                 315                 320

Ala Gly Phe Gly Val Leu Ile Ala Phe Ala Ser Tyr Asn Lys Phe Asp
                325                 330                 335

Asn Asn Cys Tyr Arg Asp Ala Leu Leu Thr Ser Ser Ile Asn Cys Ile
            340                 345                 350

Thr Ser Phe Val Ser Gly Phe Ala Ile Phe Ser Ile Leu Gly Tyr Met
            355                 360                 365

Ala His Glu His Lys Val Asn Ile Glu Asp Val Ala Thr Glu Gly Ala
            370                 375                 380

Gly Leu Val Phe Ile Leu Tyr Pro Glu Ala Ile Ser Thr Leu Ser Gly
385                 390                 395                 400

Ser Thr Phe Trp Ala Val Val Phe Phe Val Met Leu Leu Ala Leu Gly
                405                 410                 415

Leu Asp Ser Ser Met Gly Gly Met Glu Ala Val Ile Thr Gly Leu Ala
            420                 425                 430

Asp Asp Phe Gln Val Leu Lys Arg His Arg Lys Leu Phe Thr Phe Gly
            435                 440                 445

Val Thr Phe Ser Thr Phe Leu Leu Ala Leu Phe Cys Ile Thr Lys Gly
            450                 455                 460

Gly Ile Tyr Val Leu Thr Leu Leu Asp Thr Phe Ala Ala Gly Thr Ser
465                 470                 475                 480

Ile Leu Phe Ala Val Leu Met Glu Ala Ile Gly Val Ser Trp Phe Tyr
                485                 490                 495

Gly Val Asp Arg Phe Ser Asn Asp Ile Gln Gln Met Met Gly Phe Arg
                500                 505                 510

Pro Gly Leu Tyr Trp Arg Leu Cys Trp Lys Phe Val Ser Pro Ala Phe
            515                 520                 525

Leu Leu Phe Val Val Val Ser Ile Ile Asn Phe Lys Pro Leu Thr
            530                 535                 540

Tyr Asp Asp Tyr Ile Phe Pro Pro Trp Ala Asn Trp Val Gly Trp Gly
545                 550                 555                 560

Ile Ala Leu Ser Ser Met Val Leu Val Pro Ile Tyr Val Ile Tyr Lys
                565                 570                 575

Phe Leu Ser Thr Gln Gly Ser Leu Trp Glu Arg Leu Ala Tyr Gly Ile
            580                 585                 590

Thr Pro Glu Asn Glu His His Leu Val Ala Gln Arg Asp Ile Arg Gln
            595                 600                 605
```

```
Phe Gln Leu Gln His Trp Leu Ala Ile
    610                 615

<210> SEQ ID NO 4
<211> LENGTH: 602
<212> TYPE: PRT
<213> ORGANISM: rat

<400> SEQUENCE: 4

Met Asp Asn Arg Val Ser Gly Thr Thr Ser Asn Gly Glu Thr Lys Pro
1               5                   10                  15

Val Cys Pro Val Met Glu Lys Val Glu Glu Asp Gly Thr Leu Glu Arg
            20                  25                  30

Glu Gln Trp Thr Asn Lys Met Glu Phe Val Leu Ser Val Ala Gly Glu
        35                  40                  45

Ile Ile Gly Leu Gly Asn Val Trp Arg Phe Pro Tyr Leu Cys Tyr Lys
    50                  55                  60

Asn Gly Gly Gly Ala Phe Phe Ile Pro Tyr Leu Ile Phe Leu Phe Thr
65                  70                  75                  80

Cys Gly Ile Pro Val Phe Phe Leu Glu Thr Ala Leu Gly Gln Tyr Thr
                85                  90                  95

Asn Gln Gly Gly Ile Thr Ala Trp Arg Lys Ile Cys Pro Ile Phe Glu
            100                 105                 110

Gly Ile Gly Tyr Ala Ser Gln Met Ile Val Ser Leu Leu Asn Val Tyr
        115                 120                 125

Tyr Ile Val Val Leu Ala Trp Ala Leu Phe Tyr Leu Phe Ser Ser Phe
    130                 135                 140

Thr Thr Asp Leu Pro Trp Gly Ser Cys Ser His Glu Trp Asn Thr Glu
145                 150                 155                 160

Asn Cys Val Glu Phe Gln Lys Thr Asn Asn Ser Leu Asn Val Thr Ser
                165                 170                 175

Glu Asn Ala Thr Ser Pro Val Ile Glu Phe Trp Glu Arg Arg Val Leu
            180                 185                 190

Lys Ile Ser Asp Gly Ile Gln His Leu Gly Ser Leu Arg Trp Glu Leu
        195                 200                 205

Val Leu Cys Leu Leu Leu Ala Trp Ile Ile Cys Tyr Phe Cys Ile Trp
    210                 215                 220

Lys Gly Val Lys Ser Thr Gly Lys Val Val Tyr Phe Thr Ala Thr Phe
225                 230                 235                 240

Pro Tyr Leu Met Leu Val Val Leu Leu Ile Arg Gly Val Thr Leu Pro
                245                 250                 255

Gly Ala Ala Gln Gly Ile Gln Phe Tyr Leu Tyr Pro Asn Ile Thr Arg
            260                 265                 270

Leu Trp Asp Pro Gln Val Trp Met Asp Ala Gly Thr Gln Ile Phe Phe
        275                 280                 285

Ser Phe Ala Ile Cys Leu Gly Cys Leu Thr Ala Leu Gly Ser Tyr Asn
    290                 295                 300

Lys Tyr His Asn Asn Cys Tyr Arg Asp Cys Val Ala Leu Cys Ile Leu
305                 310                 315                 320

Asn Ser Ser Thr Ser Phe Val Ala Gly Phe Ala Ile Phe Ser Ile Leu
                325                 330                 335

Gly Phe Met Ser Gln Glu Gln Gly Val Pro Ile Ser Glu Val Ala Glu
            340                 345                 350

Ser Gly Pro Gly Leu Ala Phe Ile Ala Tyr Pro Arg Ala Val Val Met
        355                 360                 365
```

Leu Pro Phe Ser Pro Leu Trp Ala Cys Cys Phe Phe Met Val Val
    370                 375                 380

Leu Leu Gly Leu Asp Ser Gln Phe Val Cys Val Glu Ser Leu Val Thr
385                 390                 395                 400

Ala Leu Val Asp Met Tyr Pro Arg Val Phe Arg Lys Lys Asn Arg Arg
                405                 410                 415

Glu Ile Leu Ile Leu Ile Val Ser Val Ser Phe Phe Ile Gly Leu
            420                 425                 430

Ile Met Leu Thr Glu Gly Gly Met Tyr Val Phe Gln Leu Phe Asp Tyr
            435                 440                 445

Tyr Ala Ala Ser Gly Met Cys Leu Leu Phe Val Ala Ile Phe Glu Ser
    450                 455                 460

Leu Cys Val Ala Trp Val Tyr Gly Ala Ser Arg Phe Tyr Asp Asn Ile
465                 470                 475                 480

Glu Asp Met Ile Gly Tyr Lys Pro Trp Pro Leu Ile Lys Tyr Cys Trp
                485                 490                 495

Leu Phe Phe Thr Pro Ala Val Cys Leu Ala Thr Phe Leu Phe Ser Leu
            500                 505                 510

Ile Lys Tyr Thr Pro Leu Thr Tyr Asn Lys Lys Tyr Thr Tyr Pro Trp
            515                 520                 525

Trp Gly Asp Ala Leu Gly Trp Leu Leu Ala Leu Ser Ser Met Val Cys
    530                 535                 540

Ile Pro Ala Trp Ser Ile Tyr Lys Leu Arg Thr Leu Lys Gly Pro Leu
545                 550                 555                 560

Arg Glu Arg Leu Arg Gln Leu Val Cys Pro Ala Glu Asp Leu Pro Gln
                565                 570                 575

Lys Ser Gln Pro Glu Leu Thr Ser Pro Ala Thr Pro Met Thr Ser Leu
            580                 585                 590

Leu Arg Leu Thr Glu Leu Glu Ser Asn Cys
    595                 600

<210> SEQ ID NO 5
<211> LENGTH: 130
<212> TYPE: PRT
<213> ORGANISM: Artificial Sequence
<220> FEATURE:
<223> OTHER INFORMATION: Synthetic localization signals

<400> SEQUENCE: 5

Met Ser Lys Ser Lys Cys Ser Val Gly Leu Met Ser Ser Val Val Ala
1               5                   10                  15

Pro Ala Lys Glu Pro Asn Ala Val Gly Pro Lys Glu Val Glu Leu Ile
            20                  25                  30

Leu Val Met Glu Gln Asn Gly Val Gln Leu Thr Ser Ser Thr Leu Thr
        35                  40                  45

Asn Pro Arg Gln Ser Pro Val Glu Ala Gln Asp Arg Glu Thr Trp Gly
    50                  55                  60

Lys Lys Ile Asp Phe Leu Leu Ser Val Ile Gly Phe Ala Val Asp Leu
65                  70                  75                  80

Ala Asn Val Trp Arg Phe Pro Tyr Leu Cys Tyr Lys Asn Gly Gly Gly
                85                  90                  95

Ala Phe Leu Val Pro Tyr Leu Leu Phe Met Val Ile Ala Gly Met Pro
            100                 105                 110

Leu Phe Tyr Met Glu Leu Ala Leu Gly Gln Phe Asn Arg Glu Gly Ala
        115                 120                 125

```
Ala Gly
    130

<210> SEQ ID NO 6
<211> LENGTH: 34
<212> TYPE: PRT
<213> ORGANISM: Artificial Sequence
<220> FEATURE:
<223> OTHER INFORMATION: Synthetic localization signals

<400> SEQUENCE: 6

Lys Leu Gly Ala Ser Pro Arg Met Val Thr Val Asn Asp Cys Glu Ala
1               5                   10                  15

Lys Val Lys Gly Asp Gly Thr Ile Ser Ala Ile Thr Glu Lys Glu Thr
            20                  25                  30

His Phe

<210> SEQ ID NO 7
<211> LENGTH: 125
<212> TYPE: PRT
<213> ORGANISM: Artificial Sequence
<220> FEATURE:
<223> OTHER INFORMATION: Synthetic localization signals

<400> SEQUENCE: 7

Met Leu Leu Ala Arg Met Asn Pro Gln Val Gln Pro Glu Asn Asn Gly
1               5                   10                  15

Ala Asp Thr Gly Pro Glu Gln Pro Leu Arg Ala Arg Lys Thr Ala Glu
            20                  25                  30

Leu Leu Val Val Lys Glu Arg Asn Gly Val Gln Cys Leu Leu Ala Pro
        35                  40                  45

Arg Asp Gly Asp Ala Gln Pro Arg Glu Thr Trp Gly Lys Lys Ile Asp
    50                  55                  60

Phe Leu Leu Ser Val Val Gly Phe Ala Val Asp Leu Ala Asn Val Trp
65                  70                  75                  80

Arg Phe Pro Tyr Leu Cys Tyr Lys Asn Gly Gly Gly Ala Phe Leu Ile
                85                  90                  95

Pro Tyr Thr Leu Phe Leu Ile Ile Ala Gly Met Pro Leu Phe Tyr Met
            100                 105                 110

Glu Leu Ala Leu Gly Gln Tyr Asn Arg Glu Gly Ala Ala
        115                 120                 125

<210> SEQ ID NO 8
<211> LENGTH: 22
<212> TYPE: PRT
<213> ORGANISM: Artificial Sequence
<220> FEATURE:
<223> OTHER INFORMATION: Synthetic localization signals

<400> SEQUENCE: 8

Glu Leu Thr Ser Pro Ala Thr Pro Met Thr Ser Leu Leu Arg Leu Thr
1               5                   10                  15

Glu Leu Glu Ser Asn Cys
            20
```

TUBULO-VESICULAR STRUCTURE LOCALIZATION SIGNALS

This application is a continuation of U.S. application Ser. No. 11/999,143, filed Dec. 4, 2007 (abandoned), which claims priority benefit of U.S. Application No. 60/868,538, filed 4 Dec. 2006.

FIELD OF INVENTION

The invention relates to subcellular localization signals. In particular, the invention relates to tubulo-vesicular structure localization signals in monomeric form. The localization signals are utilized as research tools or are linked to therapeutics.

This application has subject matter related to application Ser. No. 10/682,764 (US2004/0185556, PCT/US2004/013517, WO2005/040336), Ser. No. 11/233,246, and US20040572011P (WO2005116231). Each of these patents and applications is hereby incorporated by reference.

BACKGROUND AND PRIOR ART

Drugs that act intracellularly generally enter cells by diffusion. Most drugs are small molecules because they have the ability to diffuse across tubulovesicular structures or organelle membranes to reach their site of action. To increase the bioavailability of a drug, often small molecules must be modified and/or formulated for greater solubility and/or permeability, depending on route of administration. Even small diffusible drugs may not be efficacious at their site of action. For example, multidrug resistance (MDR) may be present, which results in active efflux of drugs that enter cells with MDR. MDR often occurs in cancer cells.

In contrast to small molecules, high molecular weight compounds and polymer drugs, such as polynucleotides, polypeptides, and other macromolecules have little to no ability to diffuse across membranes. High molecular weight material is generally internalized by endocytosis. The addition of affinity binding partners to high molecular weight material can direct the high molecular weight compound to specific cells, and thereby result in increased selective uptake. However, once endocytosed, the material still remains separated from the cellular cytoplasm by a biological membrane.

Furthermore, endocytosed material is often delivered to the lysosome, where material sensitive to lysosomal enzymes is quickly degraded if steps are not taken to protect its breakdown or to facilitate escape from the lysosome. Delivery of high molecular weight compounds to their site of action at effective levels is a problem. It is therefore desirable to improve delivery to a desired subcellular compartment.

An aspect of the invention is to provide novel tubular vesicular structure localization signals by modifying one or more proteins capable of locating to the tubulo-vesicular structure of polarized cells by truncation or by amino acid substitution. Truncations, amino acid substitutions, and other modifications of known tubulo-vesicular structure-locating proteins are made to minimize endogenous biological activities other than localization. In general, the invention relates to cellular localization signals. More specifically, the invention relates to tubulovesicular structure localization signals in polarized cells. In polarized cells, such as kidney epithelial cells, which contain membranes, localization signals are selective for one of these tubulo-vesicular structure locations.

The polarized cell tubulo-vesicular structure localization signals are monomeric units that can be used separately or together for the purpose of targeting a polypeptide or other molecule of interest to a desired tubulo-vesicular structure location. Monomeric units used together exploit cooperation and synergism among individual signals in order to enhance strength and/or performance of individual signals. For example, some localization signals function at the N-terminus of a polypeptide of interest, and other localization signals function at the C-terminus of a polypeptide of interest. The signals of this invention encompass localization signals placed toward the N-terminus or C-terminus, or both the N-terminus and C-terminus of a polypeptide or other molecule of interest.

The localization signals are utilized as research tools or are linked to therapeutics. Disclosed are methods of making and using polypeptides and modified polypeptides as signals to localize therapeutics, experimental compounds, peptides, proteins and/or other macromolecules to the tubulo-vesicular structure of polarized eukaryotic cells, such as kidney epithelial cells. The polypeptides of the invention optionally include linkage to reporters, epitopes and/or other experimental or therapeutic molecules. The invention also encompasses polynucleotides encoding the localization signals and vectors comprising these polynucleotides.

DETAILED DESCRIPTION OF POLYPEPTIDE SEQUENCES

SEQ ID NOS:1-4 are full length sequences of proteins that localize to the tubulo-vesicular structure of polarized cells. These sequences have the following public database accession numbers: AAB23443, AAA40607, CAA62566, AAA40602. Each of the sequences represented by these accession numbers is incorporated by reference herein.

Specifically, the polypeptide of SEQ NO:1 is a neuronal dopamine transporter, which locates to the tubulo-vesicular structure in Madin-Darby Canine Kidney (MDCK) polarized cells when expressed therein. The polypeptide of SEQ ID NO:2 is a neuronal GABA transporter 3, which locates to the tubulo-vesicular structure in MDCK polarized cells when expressed therein. The polypeptide of SEQ ID NO:3 is a neuronal norepinephrine transporter, which locates to the tubulo-vesicular structure in MDCK polarized cells when expressed therein. The polypeptide of SEQ ID NO:4 is a neuronal GABA transporter 2, which locates to the tubulo-vesicular structure in MDCK polarized cells when expressed therein.

SEQ ID NOS:5-8 represent examples of monomeric tubulo-vesicular structure localization signals, SEQ ID NOS: 5-8 are subsequences of SEQ ID NOS:1-4, which represent examples of peptide sequences that confer tubulo-vesicular structure localization. SEQ ID NO:5 and SEQ ID NO:7 represent examples of polypeptides useful as apical and basolateral localization signals, respectively, when linked to the N-terminus of a polypeptide or other molecule of interest. SEQ ID NO:6 and SEQ ID NO:8 represent examples of polypeptides useful as apical and basolateral localization signals, respectively, when linked to the C-terminus of a polypeptide or other molecule of interest.

DETAILED DESCRIPTION OF DRAWINGS

The patent or application file contains at least one drawing executed in color. Copies of this patent or patent application publication with color drawing(s) will be provided b the Office upon request and payment of the necessary fee.

FIGS. 4A-4H show examples of gene constructs where localization signals are linked to an experimental or therapeutic polypeptide of interest, with an optional epitope tag and/or reporter.

BRIEF DESCRIPTION OF THE INVENTION

Figure 1A:
FIGS. 1A-1F show examples of localization signals linked to an experimental or therapeutic polypeptide of interest.
Figure 1B:
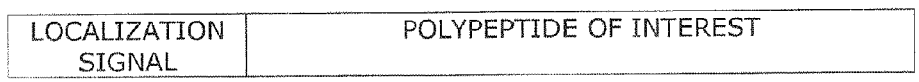
Figure 1C:
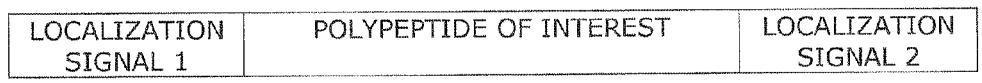
Figure 1D:
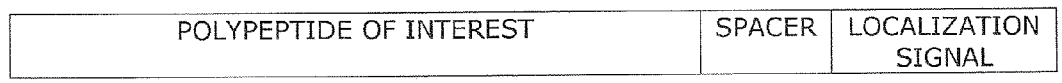
Figure 1E:
Figure 1F:
Figure 2A:
FIGS. 2A-2G show examples of localization signals linked to an epitope tag, and an experimental or therapeutic polypeptide of interest.
Figure 2B:
Figure 2C:
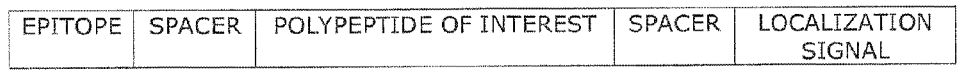
Figure 2D:
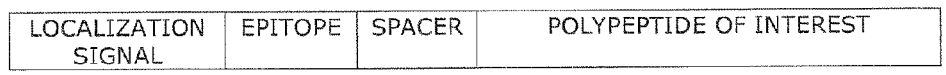
Figure 2E:
Figure 2F:
Figure 2G:
Figure 3A:
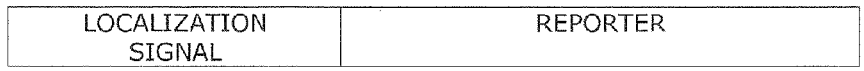
FIGS. 3A-3F show examples of localization signals linked to a reporter.
Figure 3B:
Figure 3C:
Figure 3D:
Figure 3E:
Figure 3F:

The invention relates to polarized cell tubulo-vesicular structure localization signals. Various embodiments of the tubulo-vesicular structure localization signals are represented in SEQ ID NOS:5-8. More specifically, the invention relates to monomeric localization signals used toward either the N-terminus of a polypeptide, the C-terminus of a polypeptide, or both the N-terminus and C-terminus of a polypeptide. Additionally, the invention relates to monomeric tubulo-vesicular structure localization signals comprising one or more subsequences of SEQ ID NOS:1-4 or any portion thereof. Furthermore, the invention relates to monomeric localization signals with at least about 80%, 85%, 90%, 95%, 96%, 97%, 98% and 99% sequence identity to a polypeptide comprising one or more of SEQ ID NOS:5-8 or any portion thereof. Furthermore, the invention relates to monomeric localization signals with at least about 80%, 85%, 90%, 95%, 96%, 97%, 98% and 99% sequence identity to a polypeptide comprising one or more subsequences of SEQ ID NOS:1-4.

A monomeric tubulo-vesicular structure localization signal is a polypeptide where at least a portion of the polypeptide is capable of conferring tubulo-vesicular structure location in polarized cells. A tubulo-vesicular structure localization signal functions to direct a polypeptide or other molecule of interest to the tubulo-vesicular structure.

A monomeric apical tubulo-vesicular structure localization signal functions to direct a polypeptide or other molecule of interest to the tubulo-vesicular structure of a polarized cell.

A monomeric tubulovesicular structure localization signal functions to direct a polypeptide or other molecule of interest to the tubulovesicular structure of a polarized cell.

One embodiment of the invention is a monomeric polarized cell tubulovesicular structure localization signal containing a polypeptide at least 80% identical to one of SEQ ID NOS:5-8.

Another embodiment of the invention is a monomeric localization signal containing a polypeptide at least 80% identical to one of SEQ ID NO:5 or SEQ ID NO:6.

Another embodiment of the invention is a combination localization signal containing polypeptides at least 80% identical to SEQ ID NO:5 and SEQ ID NO:6, wherein SEQ ID NO:5 is placed toward the N-terminus of a polypeptide of interest, and wherein SEQ ID NO:6 is placed toward the C-terminus of a polypeptide of interest.

Another embodiment of the invention is a monomeric localization signal containing a polypeptide at least 80% identical to one of SEQ ID NO:7 or SEQ ID NO:8.

Another embodiment of the invention is a combination localization signal containing polypeptides at least 80% identical to SEQ ID NO:7 and SEQ ID NO:8, wherein SEQ ID NO:7 is placed toward the N-terminus of a polypeptide of interest, and wherein SEQ ID NO:8 is placed toward the C-terminus of a polypeptide of interest.

Another embodiment of the invention is a localization signal containing a polypeptide at least 80% identical to one or more subsequences of SEQ ID NOS: 14.

The localization signals of the invention are optionally linked to additional molecules or amino acids that provide an epitope, a reporter, and/or an experimental or therapeutic molecule. The epitope and/or reporter and/or experimental molecule and/or therapeutic molecule may be the same molecule. The epitope and/or reporter and/or experimental molecule and/or therapeutic molecule may also be different molecules. Experimental or therapeutic molecules include but are not limited to proteins and polypeptides.

The invention also encompasses polynucleotides comprising nucleotide sequences encoding tubulo-vesicular structure localization signals. The nucleic acids of the invention are optionally linked to additional nucleotide sequences encoding polypeptides with additional features, such as an epitope, a reporter, an experimental and/or therapeutic molecule. The polynucleotides are optionally flanked by nucleotide sequences comprising restriction endonuclease sites and other nucleotides needed for restriction endonuclease activity. The flanking sequences optionally provide unique cloning sites within a vector and optionally provide directionality of subsequence cloning. Further, the nucleic acids of the invention are optionally incorporated into vector polynucleotides. The localization signals of this invention have utility in compositions for research tools and/or therapeutics.

DETAILED DESCRIPTION OF TILE INVENTION

The present invention relates to localization signals. Various embodiments of the localization signals are represented by SEQ ID NOS:5-8 or additional partial sequences of SEQ ID NOS:1-4. An example of a monomeric localization signal is the polypeptide represented by SEQ ID NO:5, SEQ ID NO:5 is a selected subsequence of wild type full length SEQ ID NO:1. Another example of a monomeric localization signal is the polypeptide represented by SEQ ID NO:6. Each of SEQ ID NOS:5-8 represents an individual tubulo-vesicular structure localization signal in monomeric form. SEQ ID NOS:5-8 are selected examples of subsequences of SEQ ID NOS:1-4, however, other subsequences of SEQ ID NOS:1-4 may also be utilized as monomeric localization signals. Monomeric subsequences of SEQ ID NOS:1-4 may be wild type subsequences. Additionally, monomeric subsequences of SEQ ID NOS:1-4 may have some amino acids different than the wild type parent. Furthermore, monomeric localization signals may have 80%, 85%, 90%, 95%, 96%, 97%, 98% or 99% sequence identity to a polypeptide comprising one or more of SEQ ID NOS:5-8. Furthermore, monomeric localization signals may have 80%, 85%, 90%, 95%, 96%, 97%, 98% and 99% sequence identity to a subsequence of SEQ ID NOS:1-4.

Monomeric localization signals may be utilized separately or in combination with each other within a polypeptide of interest to be targeted to the membrane (FIGS. 1A-1F). Monomeric units used in combination exploit synergism among individual signals in order to enhance performance of the intended localization. For example, some localization signals provide function when placed toward the N-terminus of a polypeptide of interest, and other localization signals provide function when placed toward the C-terminus of a polypeptide of interest. Therefore, SEQ ID NO:5 placed at the N-terminus of a polypeptide of interest may be used in conjunction with SEQ ID NO:6 placed at the C-terminus of a polypeptide of interest to enhance performance of either signal used separately to target the polypeptide to the tubulo-vesicular structure of polarized cells. Likewise, SEQ ID NO:7 and SEQ ID NO:8 when placed at the N-terminus and C-terminus, respectively, of a polypeptide of interest represent a pair of monomeric basolateral tubulo-vesicular structure localization signals that may be used together to target a molecule of interest to the membrane. The signals of this invention encompass localization signals linked to the N-terminus or C-terminus, or both the N-terminus and C-terminus of a polypeptide or other molecule of interest. SEQ ID NOS: 5-8 are selected examples of subsequences of SEQ ID NOS: 1-4, however, additional subsequences, wild type or mutated, may be utilized to form monomeric polarized cell tubulo-vesicular structure localization signals.

SEQ ID NOS:1-4 represent full length sequences of proteins that have tubulo-vesicular structure localization activity in polarized kidney epithelial cells. SEQ ID NOS:5-8 are subsequences of SEQ ID NOS:1-4 that are capable of conferring tubulo-vesicular structure localization. Polypeptide subsequences that are identical to their wild type parent may be used as part of a localization signal, however in one embodiment some amino acids are mutated to another amino acid, such as one of the naturally occurring amino acids including, alanine, aspartate, asparagine, cysteine, glutamate, glutamine, phenylalanine, glycine, histidine, isoleucine, leucine, lysine, methionine, proline, arginine, valine, tryptophan, serine, threonine, or tyrosine. Mutation of amino acids may be performed for various reasons including, but not limited to, minimization of undesired biological activity, introduction or removal of secondary structure in the polypeptide; disruption of protein/protein interaction; modification of charge, hydrophobicity, or stability of the polypeptide; and introduction or removal of restriction sites in the nucleic acid encoding the polypeptide.

In general, tubulo-vesicular structure localization signals are built by identifying proteins that localize to the tubulo-vesicular structure and/or specific polarized locations of the tubulo-vesicular structure such as apical and basolateral locations. Sometimes it is desirable to utilize wild type truncations. However, it is sometimes desirable to modify one or more amino acids to enhance the localization. Other reasons for modifying the wild type sequences are to remove undesired characteristics, such as enzymatic activity or modulation of an endogenous cellular function. Monomeric signals may include a tubule-vesicular structure localization sequence as well as amino acids adjacent and contiguous on either side. Monomeric signals may therefore be any length provided the monomer confers tubulo-vesicular structure localization. For example, the monomer may comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30-100 or more amino acids adjacent to the tubulo-vesicular structure localization sequence.

For example, in one embodiment, the invention comprises a polypeptide containing an amino acid sequence at least 80% identical to SEQ ID NO:5 in frame with an amino acid sequence at least 80% identical to SEQ ID NO:6.

In another embodiment, the invention comprises a polypeptide containing an amino acid sequence at least 80% identical to SEQ ID NO:7 in frame with an amino acid sequence at least 80% identical to SEQ ID NO:8.

In another embodiment, the invention comprises a tubulo-vesicular structure localization signal comprising at least one copy of a peptide selected from the group consisting of
  a) a peptide at least 80% identical to a peptide comprising amino acid residues corresponding to amino acid residues 1-145 of the amino acid sequence of SEQ ID NO:1;
  b) a peptide at least 80% identical to a peptide comprising amino acid residues corresponding to amino acid residues 1-140 of the amino acid sequence of SEQ ID NO: 1;
  c) a peptide at least 80% identical to a peptide comprising amino acid residues corresponding to amino acid residues 1-135 of the amino acid sequence of SEQ ID NO:1; and
  d) a peptide at least 80% identical to a peptide comprising amino acid residues corresponding to amino acid residues 1-130 of the amino acid sequence of SEQ ID NO: 1.

In another embodiment, the invention comprises a tubulo-vesicular structure localization signal comprising at least one copy of a peptide selected from the group consisting of:
  a) a peptide at least 80% identical to a peptide comprising amino acid residues corresponding to amino acid residues 594-627 of the amino acid sequence of SEQ ID NO:2;
  b) a peptide at least 80% identical to a peptide comprising amino acid residues corresponding to amino acid residues 591-627 of the amino acid sequence of SEQ ID NO:2;
  c) a peptide at least 80% identical to a peptide comprising amino acid residues corresponding to amino acid residues 584-627 of the amino acid sequence of SEQ ID NO:2; and
  d) a peptide at least 80% identical to a peptide comprising amino acid residues corresponding to amino acid residues 577-627 of the amino acid sequence of SEQ ID NO:2.

In another embodiment, the invention comprises a combination localization signal comprising a peptide at least 80% identical to a subsequence of SEQ ID NO:1 in frame with a peptide at least 80% identical to a subsequence of subsequence of SEQ ID NO:2.

In another embodiment, the invention comprises a localization signal comprising at least one copy of a peptide selected from the group consisting of
  a) a peptide at least 80% identical to a peptide comprising amino acid residues corresponding to amino acid residues 1-125 of the amino acid sequence of SEQ ID NO:3;
  b) a peptide at least 80% identical to a peptide comprising amino acid residues corresponding to amino acid residues 1-130 of the amino acid sequence of SEQ ID NO:3;
  c) a peptide at least 80% identical to a peptide comprising amino acid residues corresponding to amino acid residues 135 of the amino acid sequence of SEQ NO:3; and
  d) a peptide at least 80% identical to a peptide comprising amino acid residues corresponding to amino acid residues 1-140 of the amino acid sequence of SEQ ID NO:3.

In another embodiment, the invention comprises a localization signal comprising at least one copy of a peptide selected from the group consisting of:
  a) a peptide at least 80% identical to a peptide comprising amino acid residues corresponding to amino acid residues 581-602 of the amino acid sequence of SEQ ID NO:4;

b) a peptide at least 80% identical to a peptide comprising amino acid residues corresponding to amino acid residues 576-602 of the amino acid sequence of SEQ ID NO:4;

c) a peptide at least 80% identical to a peptide comprising amino acid residues corresponding to amino acid residues 573-602 of the amino acid sequence of SEQ ID NO:4; and d) a peptide at least 80% identical to a peptide comprising amino acid residues corresponding to amino acid residues 5769-602 of the amino acid sequence of SEQ ID NO:4.

In another embodiment, the invention comprises a combination localization signal comprising a peptide at least 80% identical to a subsequence of SEQ ID NO:3 in frame with a peptide at least 80% identical to a subsequence of subsequence of SEQ ID NO:4.

In another embodiment, the invention comprises a tubulovesicular structure localization signal linked to an epitope.

In another embodiment, the invention comprises a tubulovesicular structure localization signal linked to a reporter.

In another embodiment, the invention comprises a tubulovesicular structure localization signal linked to a polypeptide of interest.

In another embodiment, the invention comprises a tubulovesicular structure localization signal linked to a therapeutic molecule.

In another embodiment, the invention comprises a nucleic acid molecule comprising a polynucleotide sequence encoding a localization signal.

In another embodiment, the invention comprises a vector comprising polynucleotide sequence encoding a localization signal.

In another embodiment, the invention comprises a recombinant host cell comprising the vector containing a polynucleotide sequence encoding a localization signal.

In another embodiment, the invention comprises a method of localizing a polypeptide of interest to a tubulovesicular structure subcellular compartment in a cell comprising linking a polypeptide of interest open reading frame to a nucleic acid molecule encoding a localization signal to create a fusion protein coding sequence, and transfecting the fusion protein coding sequence into a host cell and culturing the transfected host cell under conditions suitable to produce at least one copy of the fusion protein.

As used herein, the term "tubule-vesicular structure" refers to describing novel subcellular structures) with characteristics similar to those in the figures (FIGS. 12-16) within this application.

As used herein, the terms "correspond(s) to" and "corresponding to," as they relate to sequence alignment, are intended to mean enumerated positions within a reference protein, e.g., dopamine transporter (SEQ ID NO:1), and those positions that align with the positions on the reference protein. Thus, when the amino acid sequence of a subject peptide is aligned with the amino acid sequence of a reference peptide, e.g., SEQ ID NO:1, the amino acids in the subject peptide sequence that "correspond to" certain enumerated positions of the reference peptide sequence are those that align with these positions of the reference peptide sequence, but are not necessarily in these exact numerical positions of the reference sequence. Methods for aligning sequences for determining corresponding amino acids between sequences are described below.

Another embodiment of the invention is a nucleic acid molecule comprising a polynucleotide sequence encoding at least one copy of a polarized cell tubulo-vesicular structure localization signal polypeptide.

Another embodiment of the invention is a nucleic acid molecule comprising a polynucleotide sequence encoding at least two polarized cell tubulo-vesicular structure localization signal polypeptides.

Another embodiment of the invention is a nucleic acid molecule comprising a polynucleotide sequence encoding at least two different polarized cell tubulo-vesicular structure localization signal polypeptides.

Another embodiment of the invention is a nucleic acid molecule wherein the polynucleotide sequence encodes at least a number of copies of tubulovesicular structure localization signal selected from the group consisting of 2, 3, 4, 5, 6, 7, 8, 9 or 10.

Another embodiment of the invention is a vector comprising a nucleic acid molecule encoding at least one copy of a polarized cell tubulo-vesicular structure localization signal.

Another embodiment of the invention is a recombinant host cell comprising a vector comprising a nucleic acid molecule encoding at least one copy of a tubulo-vesicular structure localization signal.

Another embodiment of the invention is a method of localizing a polypeptide to a tubulo-vesicular structure in a polarized cell comprising linking a polypeptide open reading frame to a localization signal open reading frame to create a fusion protein coding sequence, and transfecting the fusion protein coding sequence into a host cell and culturing the transfected host cell under conditions suitable to produce at least one copy of the fusion protein.

Another embodiment of the invention is a method of delivering a therapeutic molecule to a subcellular location in a cell comprising transfecting a vector comprising a nucleic acid molecule encoding at least one copy of a localization signal linked to a therapeutic molecule into a host cell and culturing the transfected host cell under conditions suitable to produce at least one copy of the localization signal containing therapeutic molecule.

The invention also relates to modified localization signals that are at least about 80%, 85%, 90% 95%, 96%, 97%, 98% or 99% identical to a reference polypeptide. A modified localization signal is used to mean a peptide that can be created by addition, deletion or substitution of one or more amino acids in the primary structure (amino acid sequence) of a localization signal protein or polypeptide. The terms "protein" and "polypeptide" and "peptide" are used interchangeably herein. The reference polypeptide is considered to be the wild type protein or a portion thereof. Thus, the reference polypeptide may be a protein whose sequence was previously modified over a wild type protein. The reference polypeptide may or may not be the wild type protein from a particular organism.

A polypeptide having an amino acid sequence at least, for example, about 95% identical to a reference an amino acid sequence is understood to mean that the amino acid sequence of the polypeptide is identical to the reference sequence except that the amino acid sequence may include up to about five modifications per each 100 amino acids of the reference amino acid sequence encoding the reference peptide. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques, (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part 1, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there exist several methods to measure identity between two polynucleotide or polypeptide sequences, the term "identity" is well known to skilled artisans (Carillo, H. & Lipton, D., Siam J Applied Math 48:1073 (1988)), Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(0:387 (1984)), BLASTP, ExPASy, BLASTN, PASTA (Atschul, S. F., et al., J Molec Biol 215:403 (1990)) and FASTDB. Examples of methods to determine identity and similarity are discussed in Michaels, G. and Clarion, R., *Current Protocols in Protein Science*, Vol 1, John Wiley & Sons, Inc. (2000), which is incorporated by reference. In one embodiment of the present invention, the algorithm used to determine identity between two or more polypeptides is BLASTP.

In another embodiment of the present invention, the algorithm used to determine identity between two or more polypeptides is FASTDB, which is based upon the algorithm of Brutlag et al. (Comp. App. Biosci. 6:237-245 (1990), incorporated by reference). In a FASTDB sequence alignment, the query and subject sequences are amino sequences. The result of sequence alignment is in percent identity. Parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the subject sequence is shorter or longer than the query sequence because of N-terminus or C-terminus additions or deletions, not because of internal additions or deletions, a manual correction can be made, because the FASTDB program does not account for N-terminus and C-terminus truncations or additions of the subject sequence when calculating percent identity. For subject sequences truncated at the N- and C-terminal ends, relative to the query sequence, the percent identity is corrected by calculating the number of amino acids of the query sequence that are N- and C-terminus to the reference sequence that are not matched/aligned, as a percent of the total amino acids of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the query (subject) sequences or the reference sequence that extend past the N- or C-termini of the reference or subject sequence, respectively, may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue subject sequence is aligned with a 100 residue reference sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 reference sequence. This time the deletions are internal deletions so there are no residues at the N- or C-termini of the subject sequence which are not matched/aligned with the query. In this case the percent identity calculated by FASTDB is not manually corrected.

The localization signals of the invention optionally comprise spacer amino acids before or after them (for example, FIGS. 1D-1F, 2C-2F and 3D-3F). The length and composition of the spacer may vary. An example of a spacer is glycine, alanine, polyglycine, or polyalanine. In addition to providing space between peptide elements, spacers can be used for the purpose of engineering restriction sites in the encoding nucleic acid and can be used for modifying secondary structure of the polypeptide encoded. The spacer amino acids may be any amino acid and are not limited to alanine, glycine.

The localization signals of the invention are optionally linked to additional molecules or amino acids that provide an epitope, a reporter, and/or an experimental or therapeutic polypeptide or molecule (FIGS. 1A-1F, 2A-2G and 3A-3F). Non-limiting examples of epitopes are FLAG™ (Kodak; Rochester, N.Y.), HA (hemagluttinin), c-Myc and His6. Non-limiting examples of reporters are alkaline phosphatase, galactosidase, peroxidase, luciferase and fluorescent proteins. Non-limiting examples of experimental proteins or polypeptides of interest are enzymes, enzyme binding partners, signalling factors, structural factors, and peptide ligands, metabolic binding factors, nucleic acid binding factors, and cellular binding factors. The epitopes, reporters and experimental or therapeutic molecules are given by way of example and without limitation. The epitope, reporter, experimental molecule and/or therapeutic molecule may be the same molecule. The epitope, reporter, experimental molecule and/or therapeutic molecule may also be different molecules.

Localization signals and optional amino acids linked thereto can be synthesized chemically or recombinantly using techniques known in the art. Chemical synthesis techniques include but are not limited to peptide synthesis which is often performed using an automated peptide synthesizer. Peptides can also be synthesized utilizing non-automated peptide synthesis methods known in the art. Recombinant techniques include insertion of localization signal encoding nucleic acids into expression vectors, wherein nucleic acid expression products are synthesized using cellular factors and processes.

Linkage of an epitope, reporter, experimental or therapeutic molecule to a localization signal can include covalent or enzymatic linkage. When the localization signal comprises material other than a polypeptide, such as a lipid or carbohydrate, a chemical reaction to link molecules may be utilized. Additionally, non-standard amino acids and amino acids modified with lipids, carbohydrates, phosphate or other molecules may be used as precursors to peptide synthesis.

The localization signals of the invention have utility as therapeutic targeting molecules. Polypeptides or proteins of interest linked to localization signals have utility as therapeutics or as subcellular tools. For example, the fusion polypeptides depicted generically in FIGS. 1A-1F and 2A-2G have utility as subcellular tools or therapeutics. Localization signal-containing gene constructs are also delivered via gene therapy. FIGS. 5B and 5C depict embodiments of gene therapy vectors for delivering and controlling polypeptide expression in vivo. Polynucleotide sequences linked to the gene construct in FIGS. 5B and 5C include genome integration domains to facilitate integration of the transgene into a viral genome and/or host genome.

Figure 5A:
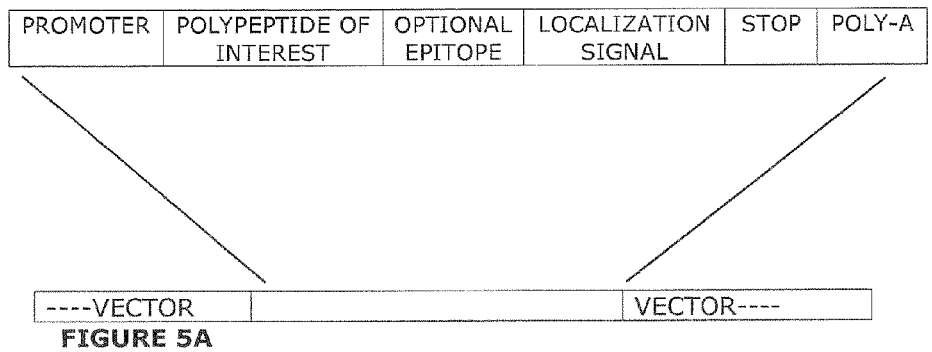
FIGS. 5A-5D show examples of vectors containing tubulovesicular structure localization signal gene constructs.
Figure 5B:
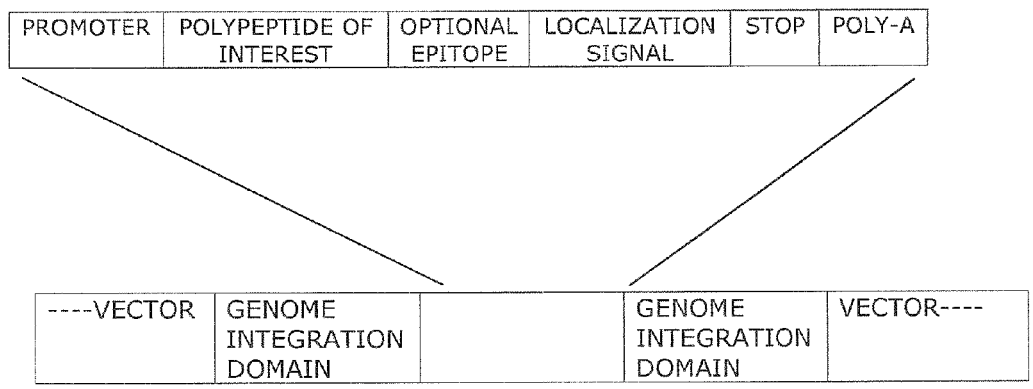
Figure 5C:
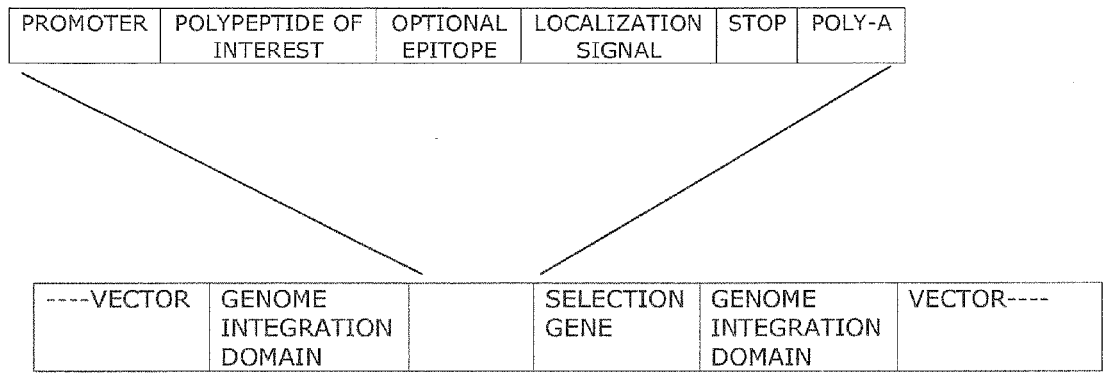

FIG. 5A shows a vector containing a tubulo-vesicular structure localization signal, optional epitope, and protein of interest gene construct, wherein the gene construct is releasable from the vector as a unit useful for generating transgenic animals. For example, the gene construct, or transgene, is released from the vector backbone by restriction endonuclease digestion. The released transgene is then injected into pronuclei of fertilized mouse eggs; or the transgene is used to transform embryonic stem cells. The vector containing a localization signal and reporter gene construct of FIG. 5A is also useful for transient transfection of the transgene, wherein the promoter and codons of the transgene are optimized for the host organism. The vector containing a gene construct of FIG. 5A is also useful for recombinant expression of polypeptides in fermentible organisms adaptable for small or large scale production, wherein the promoter and codons of the transgene are optimized for the fermentation host organism.

Figure 5D:
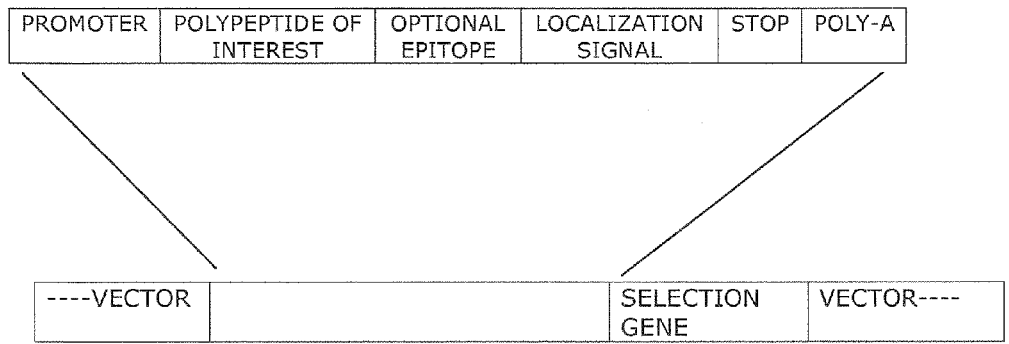
Figure 6:
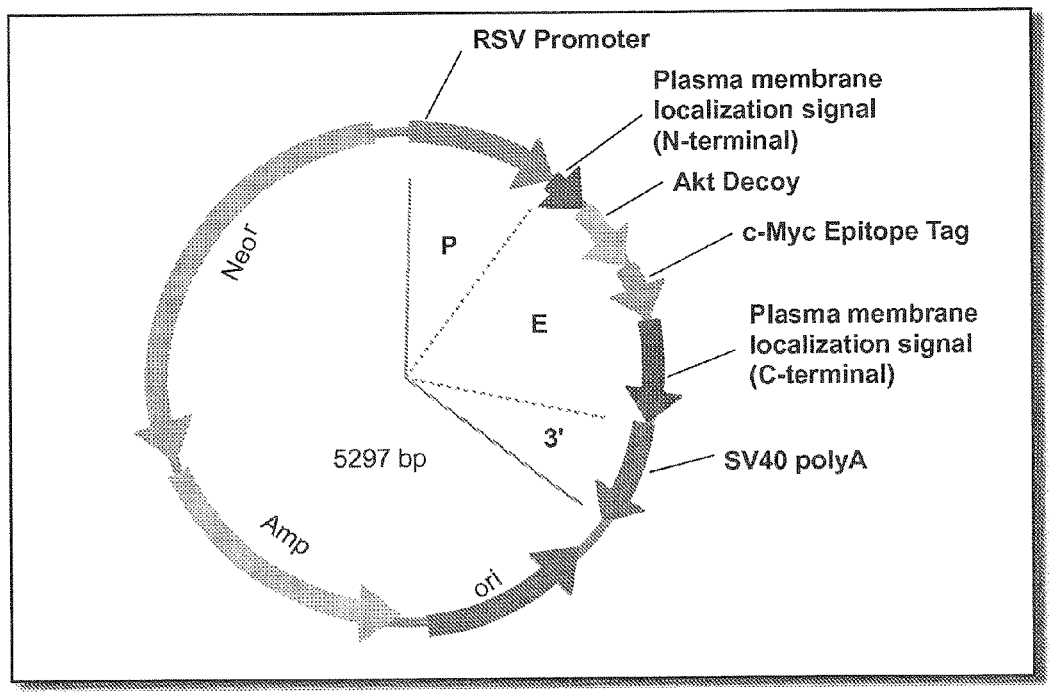
FIGS. 6-7 show examples of vectors for expression of tubulo-vesicular structure localization signals.
Figure 7:
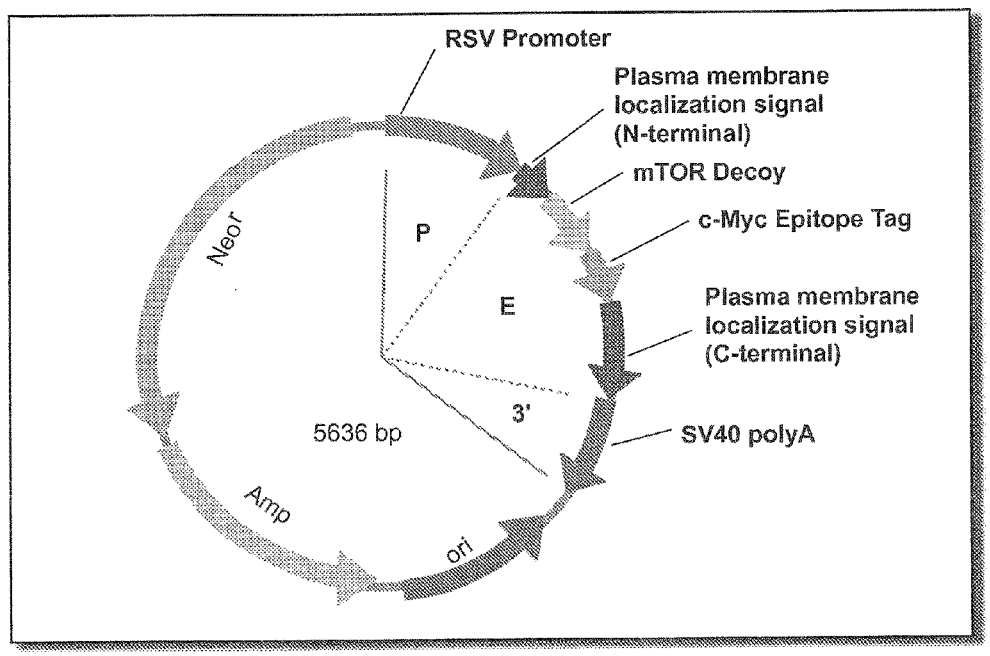
Figure 8:
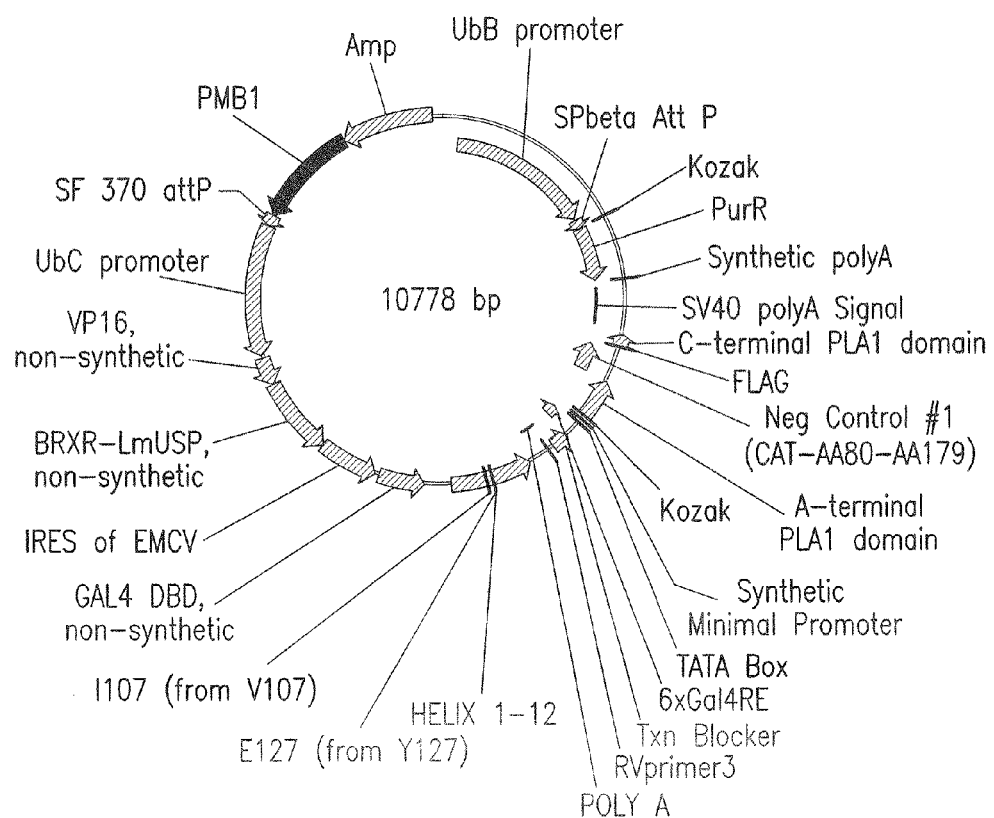
FIGS. 8-11 and 17 show additional examples of vectors for expression of tubulo-vesicular structure localization signals optionally under the control of the RheoSwitch inducible gene expression system.

FIG. 5D shows a vector containing a polarized cell tubulo-vesicular structure localization signal gene construct useful for generating stable cell lines.

The invention also encompasses polynucleotides comprising nucleotide sequences encoding polarized cell tubulo-vesicular structure localization signals. The polynucleotides of the invention are optionally linked to additional nucleotide sequences encoding epitopes, reporters and/or experimental or therapeutic molecules. Further, the nucleic acids of the invention are optionally incorporated into vector polynucleotides. The polynucleotides are optionally flanked by nucleotide sequences comprising restriction endonuclease sites and other nucleotides needed for restriction endonuclese activity. The flanking sequences optionally provide cloning sites within a vector. The restriction sites can include, but are not limited to, any of the commonly used sites in most commercially available cloning vectors. Non-limiting examples of such sites are those recognized by NsiI, ApaLI, MfeI, KpnI, BamHI, ClaI, EcoRI, EcoRV, Spa, AIM, NdeI, XbaI XhoI, SphI, NaeI, SexAI, HindIII, HpaI, and PstI restriction endonucleases. Sites for cleavage by other restriction enzymes, including homing endonucleases, are also used for this purpose. The polynucleotide flanking sequences also optionally provide directionality of subsequence cloning. It is preferred that 5' and 3' restriction endonuclease sites differ from each other so that double-stranded DNA can be directionally cloned into corresponding complementary sites of a cloning vector.

Localization signals with or without epitopes, reporters, or experimental or therapeutic proteins are alternatively synthesized by recombinant techniques. Polynucleotide expression constructs are made containing desired components and inserted into an expression vector. The expression vector is then transfected into cells and the polypeptide products are expressed and isolated. Localization signals made according to recombinant DNA techniques have utility as research tools and/or subcellular therapeutic delivery agents.

The following is an example of how polynucleotides encoding localization signals are produced. Complimentary oligonucleotides encoding the localization signals and flanking sequences are synthesized and annealed. The resulting double-stranded DNA molecule is inserted into a cloning vector using techniques known in the art. When the localization signals are placed in-frame adjacent to sequences within a transgenic gene construct that is translated into a protein product, they form part of a fusion protein when expressed in cells or transgenic animals.

Another embodiment of the invention relates to selective control of transgene expression in a desired cell or organism. The promoter portion of the recombinant gene can be a constitutive promoter, a non-constitutive promoter, a tissue-specific promoter (constitutive or non-constitutive) or a selectively controlled promoter. Different selectively controlled promoters are controlled by different mechanisms. RheoSwitch® is an inducible promoter system available from New England Biolabs (Ipswich, Mass.) (FIGS. 8-11). Temperature sensitive promoters can also be used to increase or decrease gene expression. An embodiment of the invention comprises a localization signal-containing gene construct whose expression is controlled by an inducible or repressible promoter. In one embodiment, the inducible promoter is tetracycline controllable.

Polarized cell tubule-vesicular structure localization signals and methods of making these localization signals are disclosed. Below are examples of methods of using tubulo-vesicular structure localization signals. In general, localization signals linked to epitopes, reporters, and other desired proteins or molecules are delivered via adenovirus, lentivirus, adeno-associated virus, or other viral constructs that express protein product in a cell.

EXAMPLE 1

A transgene is constructed using a human cytomegalovirus (CMV) promoter to direct expression of a fusion protein comprising SEQ ID NO:7 (LOCALIZATION SIGNAL) and green fluorescent protein (REPORTER). Such a transgene is generically represented by FIG. 4G. The transgene is transfected into cells for transient expression. Verification of expression and location is performed by visualization of the fluorescent protein by confocal microscopy.

EXAMPLE 2

A transgene is constructed using a human cytomegalovirus (CMV) promoter to direct expression of a fusion protein comprising green fluorescent protein (REPORTER) and SEQ ID NO:8 (LOCALIZATION SIGNAL). Such a transgene is generically represented by FIG. 4H. The transgene is transfected into cells for transient expression. Verification of expression and location is performed by visualization of the fluorescent protein by confocal microscopy.

EXAMPLE 3

A transgene is constructed using a human cytomegalovirus (CMV) promoter to direct expression of a fusion protein comprising SEQ. ID NO:7 (N-terminal LOCALIZATION SIGNAL 1), green fluorescent protein (REPORTER), and SEQ ID NO:8 (C-terminal LOCALIZATION SIGNAL 2). Such a transgene is generically represented by FIG. 4C. The transgene is transfected into cells for transient expression. Verification of expression and location is performed by visualization of the fluorescent protein by confocal microscopy.

EXAMPLE 4

A transgene is constructed using a human cytomegalovirus (CMV) promoter to direct expression of a fusion protein comprising SEQ ID NO:5 (LOCALIZATION SIGNAL) and green fluorescent protein (REPORTER). Such a transgene is generically represented by FIG. 4G. The transgene is transfected into cells for transient expression. Verification of expression and location is performed by visualization of the fluorescent protein by confocal microscopy.

EXAMPLE 5

A transgene is constructed using a human cytomegalovirus (CMV) promoter to direct expression of a fusion protein comprising green fluorescent protein (REPORTER) and SEQ ID NO:6 (LOCALIZATION SIGNAL). Such a transgene is generically represented by FIG. 4H. The transgene is transfected into cells for transient expression. Verification of expression and location is performed by visualization of the fluorescent protein by confocal microscopy.

EXAMPLE 6

A transgene is constructed using a human cytomegalovirus (CMV) promoter to direct expression of a fusion protein comprising SEQ ID NO:5 (N-terminal LOCALIZATION SIGNAL 1), green fluorescent protein (REPORTER), and SEQ ID NO:6 (C-terminal LOCALIZATION SIGNAL 2). Such a transgene is generically represented by FIG. 4C. The transgene is transfected into cells for transient expression. Verification of expression and location is performed by visualization of the fluorescent protein by confocal microscopy.

EXAMPLE 7

A transgene construct is built to produce a protein product with expression driven by a tissue-specific promoter. The transgene comprises a synthetic gene expression unit engineered to encode three domains. Each of these three domains is synthesized as a pair of complimentary polynucleotides that are annealed in solution, ligated and inserted into a vector. Starting at the amino-terminus, the three domains in the expression unit are nucleotide sequences that encode a kinase inhibitor, a FLAG™ epitope, and a basolateral tubulo-vesicular structure localization signal (for example, SEQ ID NO:8). Nucleotide sequences encoding a FLAG™ epitope are placed downstream of nucleotide sequences encoding the kinase inhibitor. Finally, nucleotide sequences encoding the localization signal are placed downstream of those encoding the FLAG™ epitope. The assembled gene expression unit is subsequently subcloned into an expression vector, such as that shown in FIG. 5A, and used to transiently transfect cells polarized. Verification is performed by microscopic visualization of the epitope immunoreactivity at the basolateral tubulo-vesicular structure of polarized cells.

EXAMPLE 8

Localization of a polypeptide of interest is demonstrated in vivo by making a transgene construct used to generate mice expressing a fusion protein targeted to the tubulo-vesicular structure of kidney epithelial cells. The transgene construct is shown generically in FIG. 4C. The expression unit contains nucleotides that encode SEQ ID NO:5 (N-terminal LOCALIZATION SIGNAL 1), polypeptide of interest (POLYPEPTIDE OF INTEREST), and SEQ ID NO:6 (C-terminal LOCALIZATION SIGNAL 2). This expression unit is subsequently subcloned into a vector between nucleotide sequences including a kidney epithelial cell-specific promoter and an SV40 polyadenylation signal. The completed transgene is then injected into pronuclei of fertilized mouse oocytes. The resultant pups are screened for the presence of the transgene by PCR. Transgenic founder mice are bred with wild-type mice. Heterozygous transgenic animals from at least the third generation are used for the following tests, with their non-transgenic littermates serving as controls.

Test 1: Southern blotting analysis is performed to determine the copy number. Southern blots are hybridized with a radio-labeled probe generated from a fragment of the transgene. The probe detects bands containing DNA from transgenic mice, but does not detect bands containing DNA from non-transgenic mice. Intensities of the transgenic mice bands are measured and compared with the transgene plasmid control bands to estimate copy number. This demonstrates that mice in Example 8 harbor the transgene in their genomes.

Test 2: Kidney cells are prepared for microscopic analysis. Visualization is performed using a fluorescently labeled antibody against the polypeptide of interest. This experiment demonstrates the transgene is expressed at the tubulo-vesicular structure of kidney epithelial cells in transgenic mice because the polypeptide of interest is visualized in transgenic kidney cells but not in non-transgenic tissues.

These examples demonstrate delivery of a polypeptide or other molecule of interest to a localized region of a cell for therapeutic or experimental purposes. Nucleotide sequences encoding the localization signals permit incorporation into a vector designed to deliver and express a gene product in a cell or organism. Such vectors include plasmids, cosmids, artificial chromosomes, and modified viruses. Delivery to eukaryotic cells can be accomplished in vivo or ex vivo. Ex vivo delivery methods include isolation of the intended recipient's cells or donor cells and delivery of the vector to those cells, followed by treatment of the recipient with the cells.

EXAMPLE 9

The transgene constructs haboring tubulovesicular structure localization signal are expressed and localized to the basal surface of mammalian cells (FIGS. 12-16). To demonstrate the tubulo-vesicular structure localization, the mammalian cell line MDCK (ATCC #CCL-34), canine normal kidney cells, was used. Cell were plated on poly-L-lysine coated MatTek Cultureware 24 well glass bottom plates (#P24G-1.5-13-F) at a density of 15,000 cells/cm². The cells were then transfected using Fugene6 transfection reagent (Roche) at a ratio of 1.2 μl Fugene6 reagent to 04 μg of total DNA per well. The ratio of intergrase vector to specific vector was 3:1; 03 μg of VVN-3217 to 0.1 μg of VVN859x. The transfected cells were grown at 37° C. for 3 days before induction with RSL1 at 100 nM. The cells were induced for 18 hr before fixation with 4% paraformaldehyde for 10 min. The cells were washed 3 times with PBS for 5 min per wash. Blocking was performed for 30 minutes using 5% bovine serum albumin in PBS (BSA/PBS) at room temperature followed by washing the cells as above. Primary antibodies were diluted in 1% BSA/PBS at a dilution of 1:100. VVN-8595 (FIGS. 8 and 12) and VVN-8596 (FIGS. 9 and 13) were stained with mouse-anti-FLAG (Sigma) and VVN-8598 (FIGS. 10 and 14) and VVN-8599 (FIGS. 11, 15 and 16) were stained with rat-anti-HA (Roche) for 1 hour at room temperature. After the cells were washed as above and secondary antibodies were added at 1:1000 diluted in 1% BSA/PBS for 1 hour. VVN-8595 (FIGS. 8 and 12) and VVN-8596 (FIGS. 9 and 13) were stained with goat-anti-mouse Alexa488 and VVN-8598 (FIGS. 10 and 14) and VVN-8599 (FIGS. 11, 15 and 16) were stained with rabbit-anti-rat Alexa488. The cells were washed as above and stained with DAPI to stain the nucleus of the MDCK cells for 5 minutes followed by washing as above. The cells were then imaged on the Zeiss Observer in a Z-stack at 63×.

Disclosed are polarized cell tubulo-vesicular structure localization signals and methods of making and using these localization signals. The localization signals are utilized as research tools or as therapeutic delivery agents. The invention includes linking polypeptides or other molecules of interest to cellular localization signals for subcellular therapeutics.

What is claimed is:

1. An isolated nucleic acid molecule comprising a polynucleotide sequence encoding a fusion protein comprising a polypeptide of interest, wherein the polypeptide of interest is functionally linked to a heterologous tubulovesicular localization signal polypeptide and wherein said tubulovesicular localization signal polypeptide is selected from the group consisting of:
 (i) amino acid residues 1-145 of SEQ ID NO:1;
 (ii) amino acid residues 1-140 of SEQ ID NO:1;
 (iii) amino acid residues 1-135 of SEQ ID NO:1; and (iv) amino acid residues 1-130 of SEQ ID NO:1, wherein said tubulovesicular localization signal directs the polypeptide encoded by said polynucleotide to a tubulovesicular structure subcellular compartment in a cell.

2. The isolated nucleic acid molecule of claim 1, wherein said polypeptide of interest is a therapeutic molecule.

3. The isolated nucleic acid molecule of claim 1, wherein said polynucleotide further encodes an epitope.

4. The isolated nucleic acid molecule of claim 1, wherein said polynucleotide further encodes spacer amino acids.

5. The isolated nucleic acid molecule of claim 1, wherein said polynucleotide further encodes a reporter.

6. The isolated nucleic acid molecule of claim 1, wherein said polynucleotide further encodes an epitope and spacer amino acids.

7. A vector comprising the isolated nucleic acid molecule of claim 1.

8. A recombinant host cell comprising the isolated nucleic acid molecule of claim 1.

9. A recombinant host cell comprising the vector of claim 7.

10. The recombinant host cell of claim 9 wherein said recombinant host cell is a mammalian cell.

11. The recombinant host cell of claim 9, wherein said recombinant host cell is a kidney epithelial cell.

12. The isolated nucleic acid molecule of claim 1, wherein the encoded tubulovesicular localization signal peptide is linked to the N-terminus of the encoded polypeptide of interest.

13. The isolated nucleic acid molecule of claim 1, wherein the encoded tubulovesicular localization signal peptide is linked to the C-terminus of the encoded polypeptide of interest.

14. The isolated nucleic acid molecule of claim 12 wherein the encoded tubulovesicular localization signal peptide is linked to the C-terminus of the encoded polypeptide of interest.

15. The isolated nucleic acid molecule of claim 1, wherein said polynucleotide encodes spacer amino acids between said polypeptide of interest and said tubulovesicular localization signal peptide.

16. A method of localizing a polypeptide of interest to a tubulo-vesicular structure subcellular compartment in a cell, the method comprising:
(a) transfecting the isolated nucleic acid molecule of claim 1 into a host cell; and
(b) culturing the transfected host cell under conditions suitable to produce at least one copy of the polypeptide encoded by said polynucleotide.

* * * * *

UNITED STATES PATENT AND TRADEMARK OFFICE
CERTIFICATE OF CORRECTION

| | | |
|---|---|---|
| PATENT NO. | : 8,993,742 B2 | Page 1 of 4 |
| APPLICATION NO. | : 12/973624 | |
| DATED | : March 31, 2015 | |
| INVENTOR(S) | : Thomas D. Reed | |

It is certified that error appears in the above-identified patent and that said Letters Patent is hereby corrected as shown below:

IN THE DRAWINGS

Figure 9:
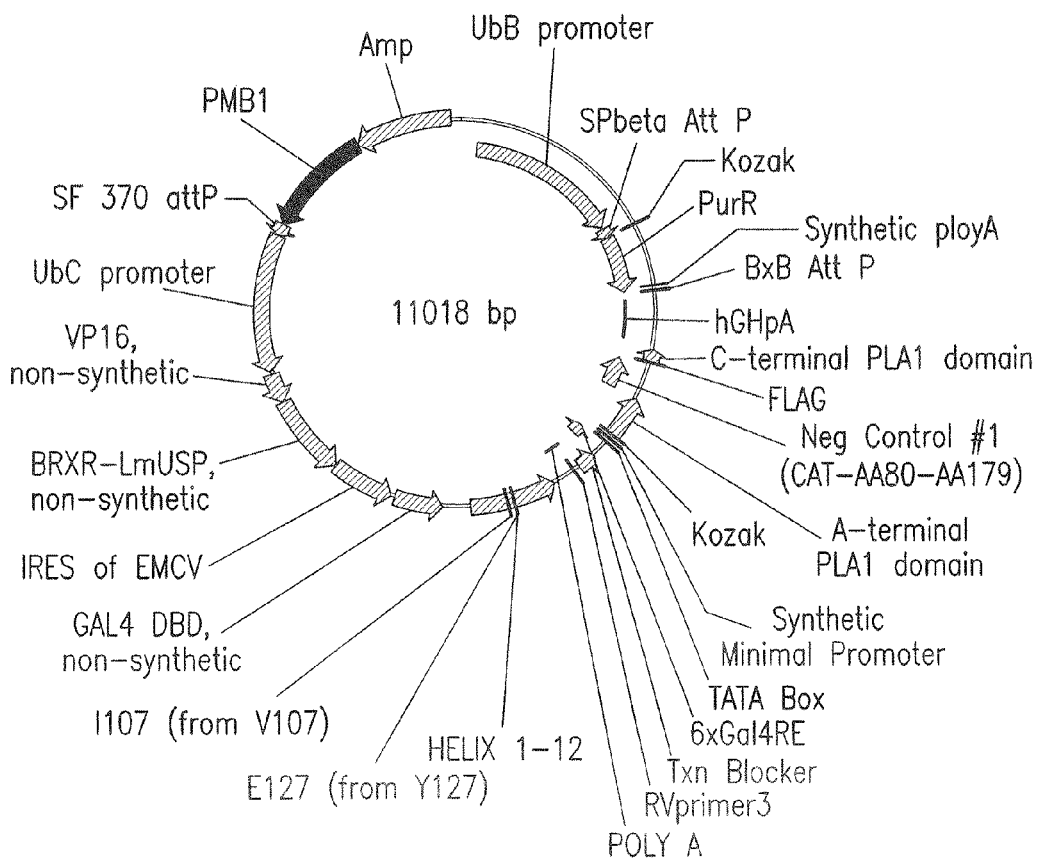
Figure 10:
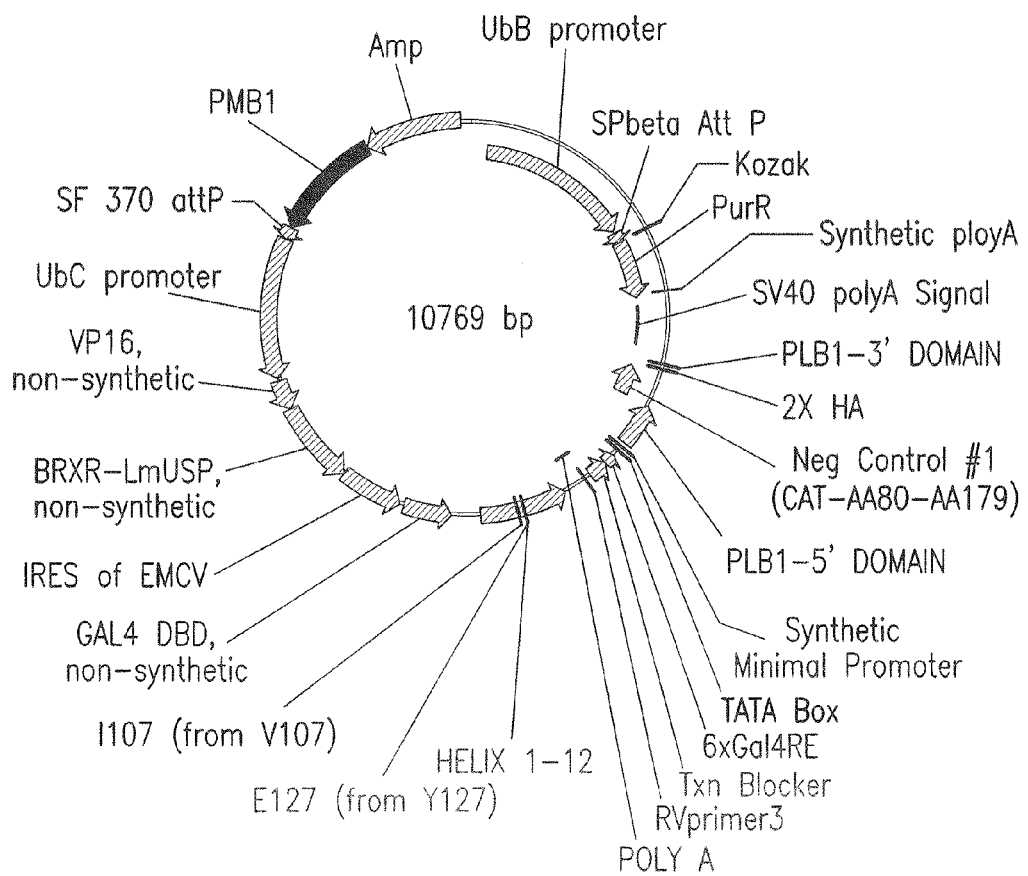
Figure 11:
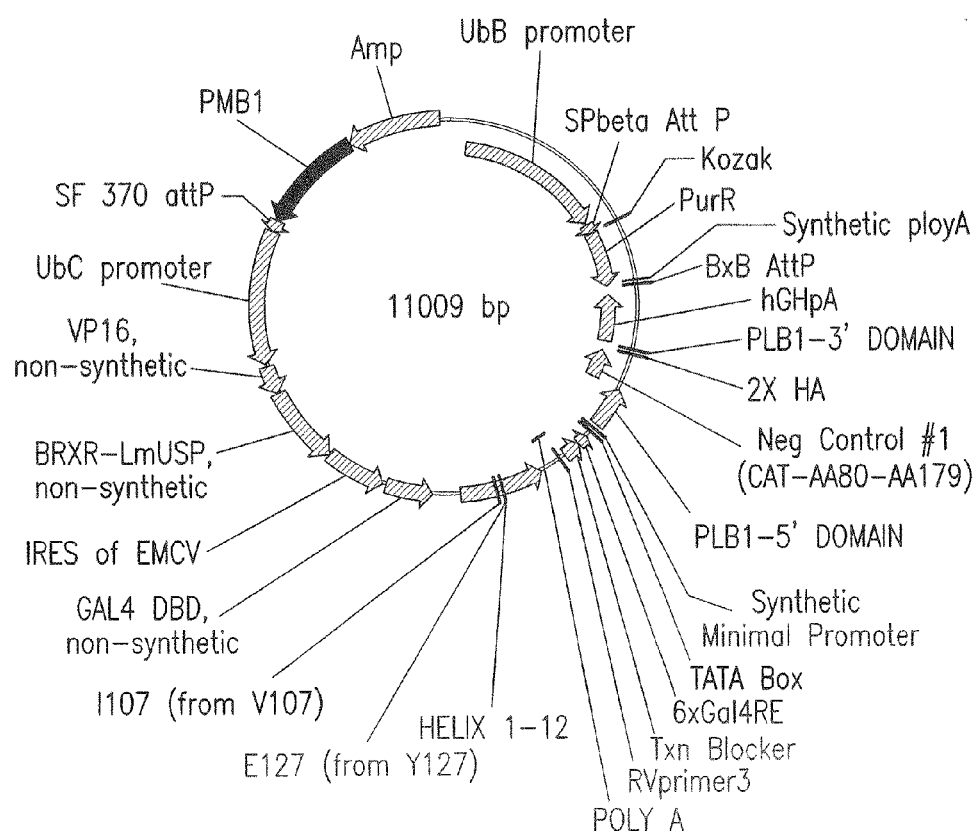
Figure 12:
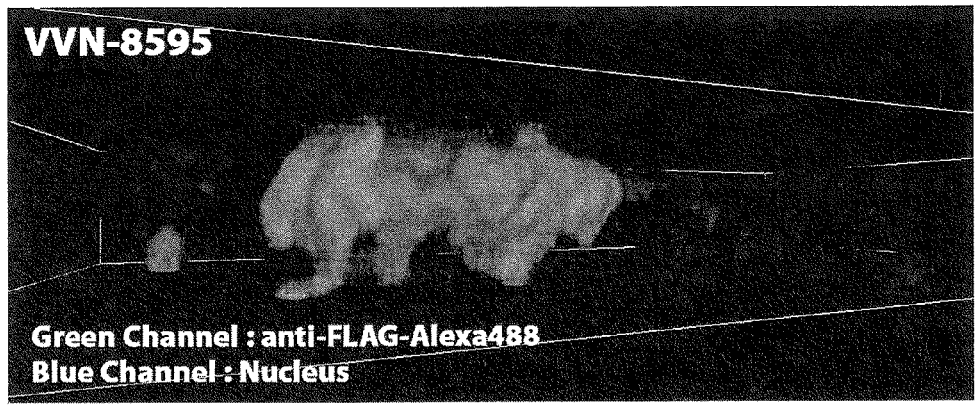
FIGS. 12-16 show examples of microscopic images, which demonstrate the expression of tubulo-vesicular structure localization signals localized to the tubulo-vesicular structure.
Figure 13:
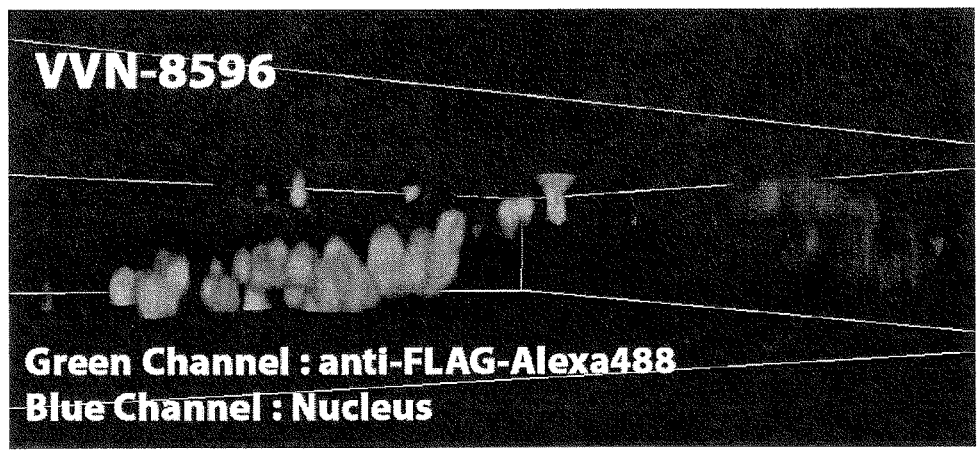
Figure 14:
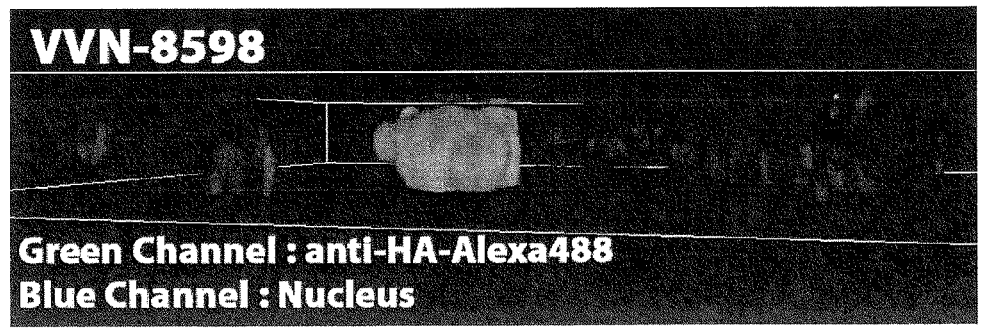
Figure 15:
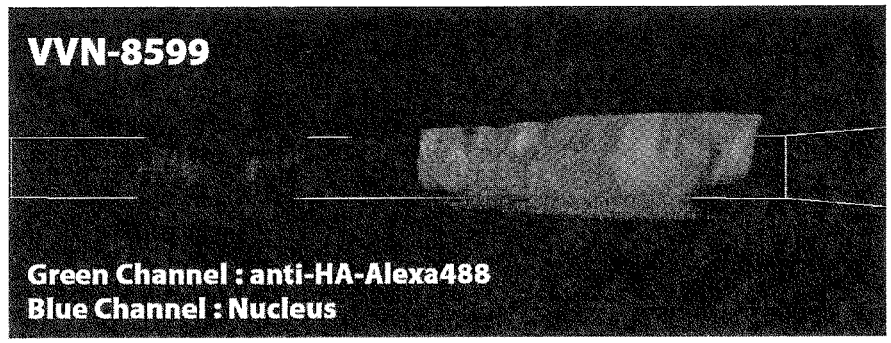
Figure 16:
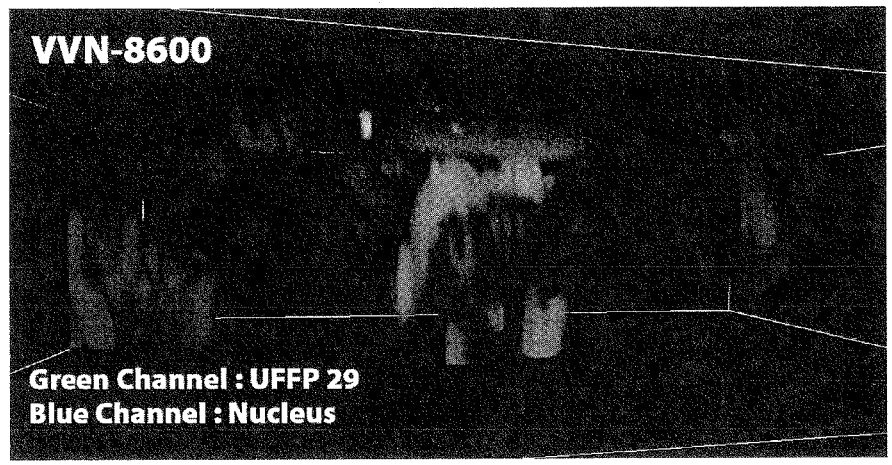
Figure 17:
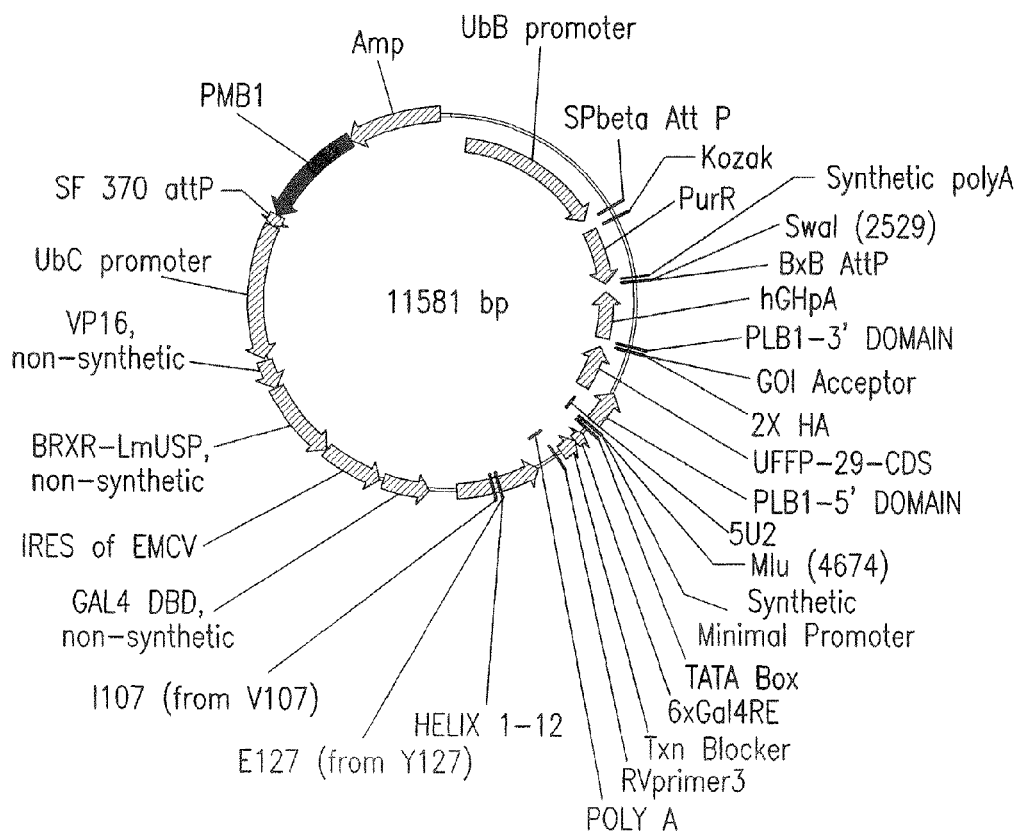
Figure 9:
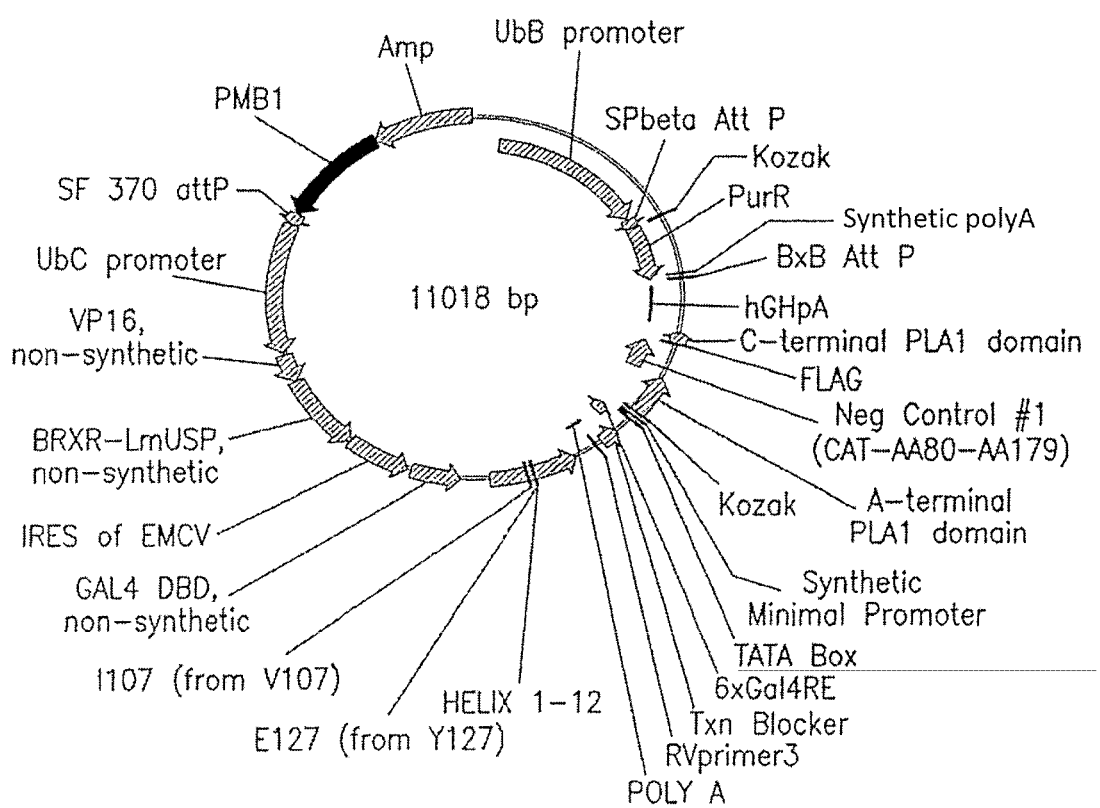
Figure 10:
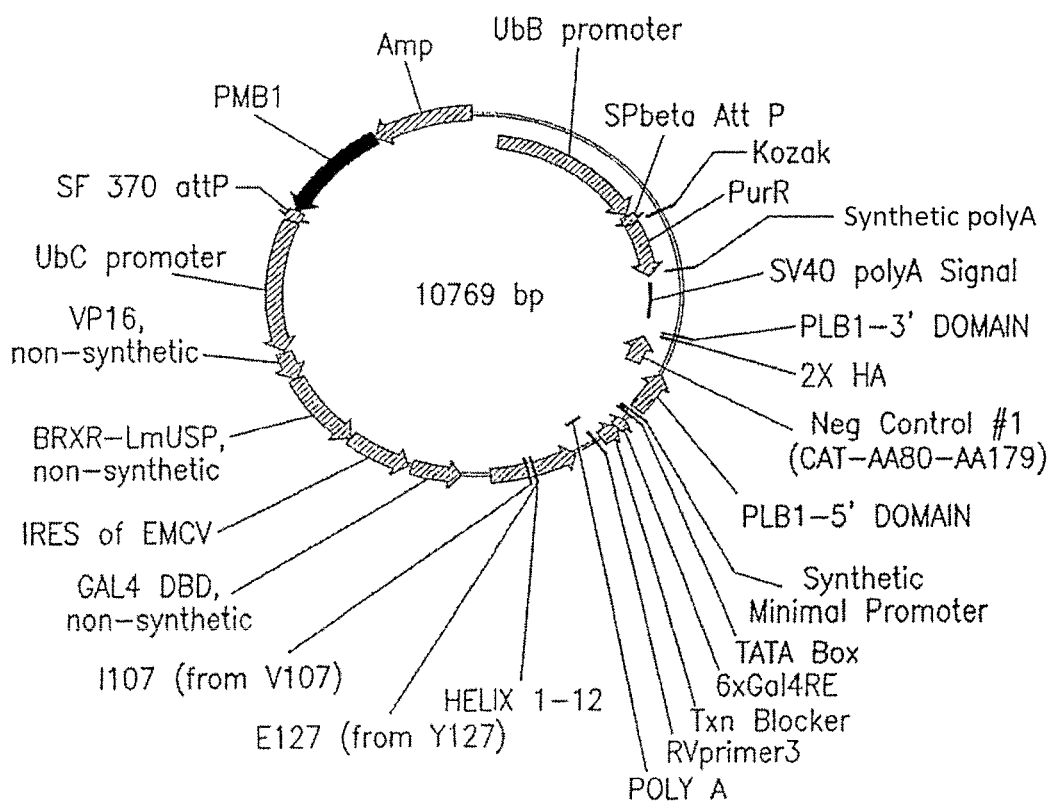
Figure 11:
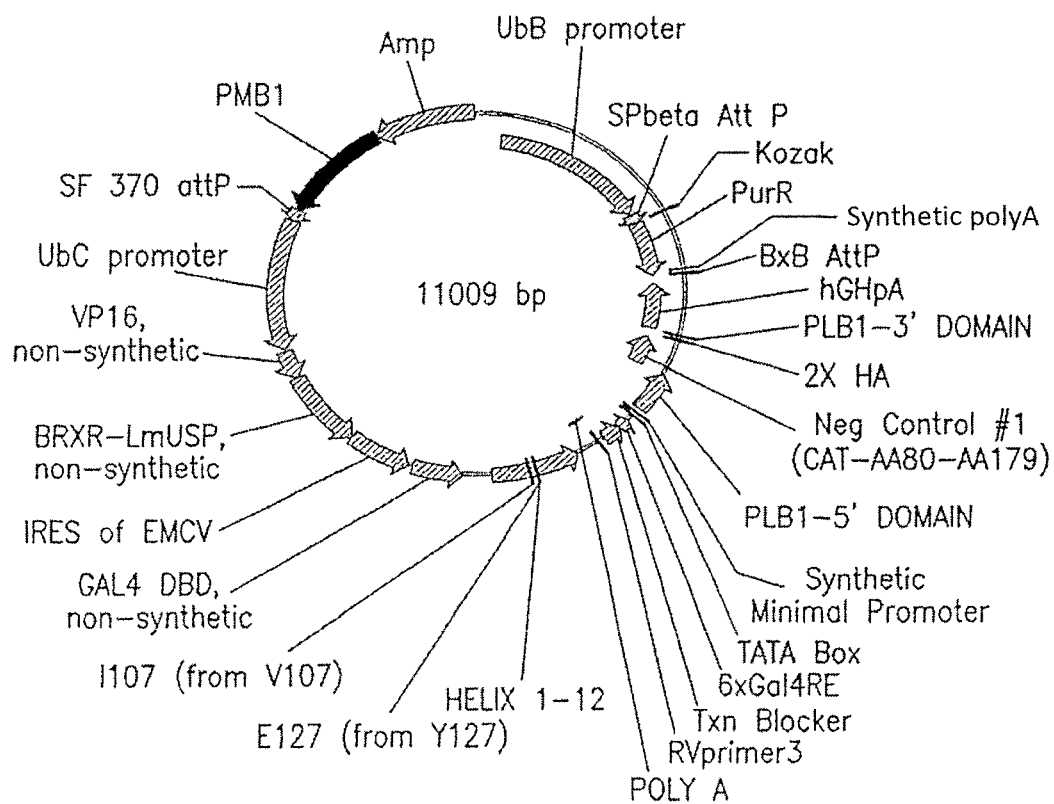

Please replace Figures 9-11 with attached Replacement Figures 9-11.

Signed and Sealed this
Twentieth Day of October, 2015

Michelle K. Lee
*Director of the United States Patent and Trademark Office*

VVN-8596 RG2+(PLA1-5'+CAT+FLAG+PLA1-3')+hGHpA